(12) United States Patent
Shin et al.

(10) Patent No.: US 12,213,378 B2
(45) Date of Patent: Jan. 28, 2025

(54) COMPOUND FOR ORGANIC OPTOELECTRONIC DEVICE, ORGANIC OPTOELECTRONIC DEVICE, AND DISPLAY DEVICE

(71) Applicant: SAMSUNG SDI CO., LTD., Yongin-si (KR)

(72) Inventors: Chang Ju Shin, Suwon-si (KR); Hyung Sun Kim, Suwon-si (KR); Dong Wan Ryu, Suwon-si (KR); Jongwoo Won, Suwon-si (KR); Hanill Lee, Suwon-si (KR); Jinseok Jang, Suwon-si (KR); Ho Kuk Jung, Suwon-si (KR); Dongkyu Ryu, Suwon-si (KR); Hyunji Yoo, Suwon-si (KR); Mijin Lee, Suwon-si (KR); Sung-Hyun Jung, Suwon-si (KR)

(73) Assignee: SAMSUNG SDI CO., LTD., Yongin-si (KR)

( * ) Notice: Subject to any disclaimer, the term of this patent is extended or adjusted under 35 U.S.C. 154(b) by 749 days.

(21) Appl. No.: 17/420,200

(22) PCT Filed: Nov. 22, 2019

(86) PCT No.: PCT/KR2019/016166
§ 371 (c)(1),
(2) Date: Jul. 1, 2021

(87) PCT Pub. No.: WO2020/145508
PCT Pub. Date: Jul. 16, 2020

(65) Prior Publication Data
US 2022/0069234 A1    Mar. 3, 2022

(30) Foreign Application Priority Data
Jan. 10, 2019 (KR) .................. 10-2019-0003517

(51) Int. Cl.
*H01L 51/50* (2006.01)
*C07D 403/14* (2006.01)
(Continued)

(52) U.S. Cl.
CPC ....... *H10K 85/6572* (2023.02); *C07D 403/14* (2013.01); *C07D 405/14* (2013.01);
(Continued)

(58) Field of Classification Search
None
See application file for complete search history.

(56) References Cited

U.S. PATENT DOCUMENTS

| | | | |
|---|---|---|---|
| 5,061,569 | A | 10/1991 | Vanslyke et al. |
| 2010/0187977 | A1 | 7/2010 | Kai et al. |

(Continued)

FOREIGN PATENT DOCUMENTS

| | | |
|---|---|---|
| CN | 101511834 A | 8/2009 |
| CN | 101641340 A | 2/2010 |

(Continued)

OTHER PUBLICATIONS

Chinese Office action and Search Report dated Dec. 19, 2023.
(Continued)

*Primary Examiner* — Gregory D Clark
(74) *Attorney, Agent, or Firm* — Lee IP Law, P.C.

(57) ABSTRACT

Disclosed are a compound for an organic optoelectronic device represented by Chemical Formula 1, and an organic optoelectronic device and a display device including the same. Details of Chemical Formula 1 are as defined in the specification.

9 Claims, 1 Drawing Sheet

(51) Int. Cl.
  *C07D 405/14* (2006.01)
  *C07D 487/04* (2006.01)
  *C09K 11/06* (2006.01)
  *H10K 85/60* (2023.01)
  *H10K 50/11* (2023.01)
  *H10K 101/00* (2023.01)
  *H10K 101/10* (2023.01)

(52) U.S. Cl.
  CPC .......... *C07D 487/04* (2013.01); *C09K 11/06* (2013.01); *H10K 85/654* (2023.02); *H10K 85/6574* (2023.02); *C09K 2211/1018* (2013.01); *H10K 50/11* (2023.02); *H10K 2101/10* (2023.02); *H10K 2101/90* (2023.02)

(56) References Cited

U.S. PATENT DOCUMENTS

| | | | |
|---|---|---|---|
| 2015/0126736 | A1 | 5/2015 | Cho et al. |
| 2017/0069848 | A1 | 3/2017 | Zeng et al. |
| 2017/0317293 | A1 | 11/2017 | Kim et al. |
| 2020/0079735 | A1 | 3/2020 | Ma et al. |
| 2020/0212314 | A1 | 7/2020 | Numata et al. |
| 2021/0135118 | A1 | 5/2021 | Son et al. |

FOREIGN PATENT DOCUMENTS

| | | |
|---|---|---|
| CN | 104271702 A | 1/2015 |
| CN | 105745200 A | 7/2016 |
| CN | 106565433 A | 4/2017 |
| CN | 107954922 A | 4/2018 |
| CN | 108358891 A | 8/2018 |
| CN | 108373463 A | 8/2018 |
| CN | 110869364 A | 3/2020 |
| CN | 110890472 A | 3/2020 |
| CN | 111384300 A | 7/2020 |
| EP | 2787549 A1 | 10/2014 |
| JP | 1993-009471 A | 1/1993 |
| JP | 1995-126615 A | 5/1995 |
| JP | 1998-095973 A | 4/1998 |
| JP | 2013-035752 A | 2/2013 |
| JP | 2017-501127 A | 1/2017 |
| JP | 2019-119723 A | 7/2019 |
| KR | 10-2006-0073541 A | 6/2006 |
| KR | 10-2011-0086043 A | 7/2011 |
| KR | 10-2012-0116282 A | 10/2012 |
| KR | 10-2012-0122812 A | 11/2012 |
| KR | 10-2013-0011405 A | 1/2013 |
| KR | 10-2014-0082351 A | 7/2014 |
| KR | 10-2014-0085111 A | 7/2014 |
| KR | 10-2014-0096182 A | 8/2014 |
| KR | 10-2014-0106631 A | 9/2014 |
| KR | 10-2015-0064878 A | 6/2015 |
| KR | 10-2016-0004466 A | 1/2016 |
| KR | 10-2016-0006629 A | 1/2016 |
| KR | 10-2018-0020577 A | 2/2018 |
| KR | 10-2018-0063708 A | 6/2018 |
| KR | 2018063708 * | 6/2018 ............ H01L 51/00 |
| KR | 10-2019-0004517 A | 1/2019 |
| KR | 10-2019-0064510 A | 6/2019 |
| KR | 10-2019-0086347 A | 7/2019 |
| WO | WO 1995/09147 A1 | 4/1995 |
| WO | WO 2003/078541 A1 | 9/2003 |
| WO | WO 2003/080760 A1 | 10/2003 |
| WO | WO 2008/056746 A1 | 5/2008 |
| WO | WO 2010/043693 A1 | 4/2010 |
| WO | WO 2015/084021 A1 | 6/2015 |
| WO | WO 2019/009591 A1 | 1/2019 |

OTHER PUBLICATIONS

Japanese Office action dated Jun. 28, 2022.
European Search Report dated Jul. 11, 2022.
International Search Report dated Mar. 16, 2020 for PCT/KR2019/016166.
Office Action (including a search report) dated Jul. 16, 2024, of the corresponding Chinese Patent Application No. 201980088485.5.

* cited by examiner

【Figure 1】
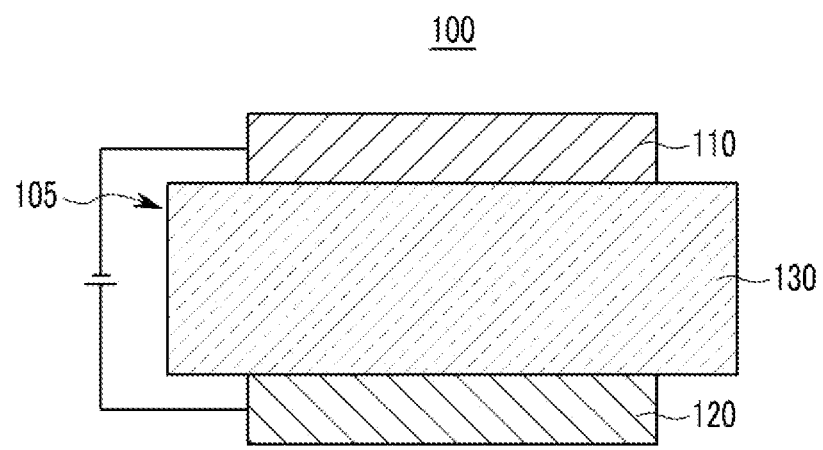
【Figure 2】
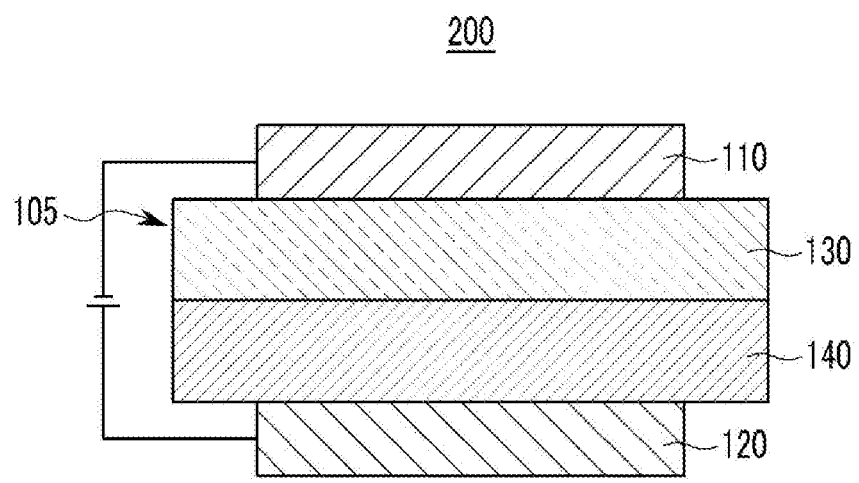

COMPOUND FOR ORGANIC OPTOELECTRONIC DEVICE, ORGANIC OPTOELECTRONIC DEVICE, AND DISPLAY DEVICE

CROSS REFERENCE TO RELATED APPLICATIONS

This is the U.S. national phase application based on PCT Application No. PCT/KR2019/016166, filed Nov. 22, 2019, which is based on Korean Patent Application No. 10-2019-0003517, filed Jan. 10, 2019, the entire contents of all of which are hereby incorporated by reference.

TECHNICAL FIELD

A compound for an organic optoelectronic device, an organic optoelectronic device, and a display device are disclosed.

BACKGROUND ART

An organic optoelectronic device (organic optoelectronic diode) is a device that converts electrical energy into photoenergy, and vice versa.

An organic optoelectronic device may be classified as follows in accordance with its driving principles. One is a photoelectric device where excitons generated by photoenergy are separated into electrons and holes and the electrons and holes are transferred to different electrodes respectively and electrical energy is generated, and the other is a light emitting device to generate photoenergy from electrical energy by supplying a voltage or a current to electrodes.

Examples of the organic optoelectronic device include an organic photoelectric device, an organic light emitting diode, an organic solar cell, and an organic photoconductor drum.

Among them, the organic light emitting diode (OLED) has recently drawn attention due to an increase in demand for flat panel displays. The organic light emitting diode converts electrical energy into light, and the performance of organic light emitting diode is greatly influenced by the organic materials disposed between electrodes.

DISCLOSURE

Technical Problem

An embodiment provides a compound for an organic optoelectronic device capable of realizing an organic optoelectronic device having high efficiency and long life-span.

Another embodiment provides an organic optoelectronic device including the compound for an organic optoelectronic device.

Another embodiment provides a display device including the organic optoelectronic device.

Technical Solution

According to an embodiment, a compound for an organic optoelectronic device represented by Chemical Formula 1 is provided.

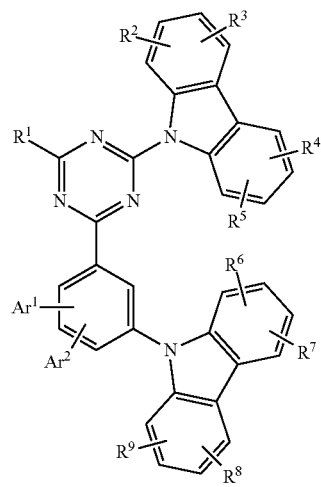

[Chemical Formula 1]

In Chemical Formula 1,
$R^1$ is a C6 to C20 aryl group that is substituted or unsubstituted with a C1 to C5 alkyl group or C6 to C12 aryl group, a substituted or unsubstituted dibenzofuranyl group that is substituted or unsubstituted with a C6 to C12 aryl group, or a dibenzothiophenyl group that is substituted or unsubstituted with a C6 to C12 aryl group,
$R^2$ to $R^9$ are each independently hydrogen, deuterium, a cyano group, a halogen, a substituted or unsubstituted amine group, a substituted or unsubstituted C1 to C30 alkyl group, a substituted or unsubstituted C6 to C30 aryl group, a substituted or unsubstituted C2 to C30 heterocyclic group, or a combination thereof, and
$Ar^1$ and $Ar^2$ are each independently hydrogen, deuterium, or a C6 to C20 aryl group.

According to another embodiment, an organic optoelectronic device includes an anode and a cathode facing each other, and at least one organic layer disposed between the anode and the cathode, wherein the organic layer includes the aforementioned compound for an organic optoelectronic device.

According to another embodiment, a display device including the organic optoelectronic device is provided.

Advantageous Effects

An organic optoelectronic device having high efficiency and a long life-span may be realized.

DESCRIPTION OF THE DRAWINGS

FIGS. 1 and 2 are cross-sectional views illustrating organic light emitting diodes according to each embodiment.

DESCRIPTION OF SYMBOLS

100, 200: organic light emitting diode
105: organic layer
110: cathode
120: anode
130: light emitting layer
140: hole auxiliary layer

MODE FOR INVENTION

Hereinafter, embodiments of the present invention are described in detail. However, these embodiments are exemplary, the present invention is not limited thereto and the present invention is defined by the scope of claims.

In the present specification, when a definition is not otherwise provided, "substituted" refers to replacement of at least one hydrogen of a substituent or a compound by deuterium, a halogen, a hydroxyl group, an amino group, a substituted or unsubstituted C1 to C30 amine group, a nitro group, a substituted or unsubstituted C1 to C40 silyl group, a C1 to C30 alkyl group, a C1 to C10 alkylsilyl group, a C6 to C30 arylsilyl group, a C3 to C30 cycloalkyl group, a C3 to C30 heterocycloalkyl group, a C6 to C30 aryl group, a C2 to C30 heteroaryl group, a C1 to C20 alkoxy group, a C1 to C10 trifluoroalkyl group, a cyano group, or a combination thereof.

In one example of the present invention, "substituted" refers to replacement of at least one hydrogen of a substituent or a compound by deuterium, a C1 to C30 alkyl group, a C1 to C10 alkylsilyl group, a C6 to C30 arylsilyl group, a C3 to C30 cycloalkyl group, a C3 to C30 heterocycloalkyl group, a C6 to C30 aryl group, a C2 to C30 heteroaryl group, or a cyano group. In addition, in specific examples of the present invention, "substituted" refers to replacement of at least one hydrogen of a substituent or a compound by deuterium, a C1 to C20 alkyl group, a C6 to C30 aryl group, or a cyano group. In addition, in specific examples of the present invention, "substituted" refers to replacement of at least one hydrogen of a substituent or a compound by deuterium, a C1 to C5 alkyl group, or a C6 to C12 aryl group. In addition, in specific examples of the present invention, "substituted" refers to replacement of at least one hydrogen of a substituent or a compound by a methyl group, an ethyl group, a phenyl group, a biphenyl group, or a naphthyl group.

In the present specification, when a definition is not otherwise provided, "hetero" refers to one including one to three heteroatoms selected from N, O, S, P, and Si, and remaining carbons in one functional group.

In the present specification, "aryl group" refers to a group including at least one hydrocarbon aromatic moiety, and may include a group in which all elements of the hydrocarbon aromatic moiety have p-orbitals which form conjugation, for example a phenyl group, a naphthyl group, and the like, a group in which two or more hydrocarbon aromatic moieties may be linked by a sigma bond, for example a biphenyl group, a terphenyl group, a quarterphenyl group, and the like, and a group in which two or more hydrocarbon aromatic moieties are fused directly or indirectly to provide a non-aromatic fused ring, for example a fluorenyl group, and the like.

The aryl group may include a monocyclic, polycyclic or fused ring polycyclic (i.e., rings sharing adjacent pairs of carbon atoms) functional group.

In the present specification, "heterocyclic group" is a generic concept of a heteroaryl group, and may include at least one heteroatom selected from N, O, S, P, and Si instead of carbon (C) in a cyclic compound such as an aryl group, a cycloalkyl group, a fused ring thereof, or a combination thereof. When the heterocyclic group is a fused ring, the entire ring or each ring of the heterocyclic group may include one or more heteroatoms.

For example, "heteroaryl group" refers to an aryl group including at least one heteroatom selected from N, O, S, P, and Si. Two or more heteroaryl groups are linked by a sigma bond directly, or when the heteroaryl group includes two or more rings, the two or more rings may be fused. When the heteroaryl group is a fused ring, each ring may include one to three heteroatoms.

More specifically, the substituted or unsubstituted C6 to C30 aryl group may be a substituted or unsubstituted phenyl group, a substituted or unsubstituted naphthyl group, a substituted or unsubstituted anthracenyl group, a substituted or unsubstituted phenanthrenyl group, a substituted or unsubstituted naphthacenyl group, a substituted or unsubstituted pyrenyl group, a substituted or unsubstituted biphenyl group, a substituted or unsubstituted p-terphenyl group, a substituted or unsubstituted m-terphenyl group, a substituted or unsubstituted o-terphenyl group, a substituted or unsubstituted chrysenyl group, a substituted or unsubstituted triphenylene group, a substituted or unsubstituted perylenyl group, a substituted or unsubstituted fluorenyl group, a substituted or unsubstituted indenyl group, or a combination thereof, but is not limited thereto.

More specifically, the substituted or unsubstituted C2 to C30 heterocyclic group may be a substituted or unsubstituted furanyl group, a substituted or unsubstituted thiophenyl group, a substituted or unsubstituted pyrrolyl group, a substituted or unsubstituted pyrazolyl group, a substituted or unsubstituted imidazolyl group, a substituted or unsubstituted triazolyl group, a substituted or unsubstituted oxazolyl group, a substituted or unsubstituted thiazolyl group, a substituted or unsubstituted oxadiazolyl group, a substituted or unsubstituted thiadiazolyl group, a substituted or unsubstituted pyridyl group, a substituted or unsubstituted pyrimidinyl group, a substituted or unsubstituted pyrazinyl group, a substituted or unsubstituted triazinyl group, a substituted or unsubstituted benzofuranyl group, a substituted or unsubstituted benzothiophenyl group, a substituted or unsubstituted benzimidazolyl group, a substituted or unsubstituted indolyl group, a substituted or unsubstituted quinolinyl group, a substituted or unsubstituted isoquinolinyl group, a substituted or unsubstituted quinazolinyl group, a substituted or unsubstituted quinoxalinyl group, a substituted or unsubstituted naphthyridinyl group, a substituted or unsubstituted benzoxazinyl group, a substituted or unsubstituted benzthiazinyl group, a substituted or unsubstituted acridinyl group, a substituted or unsubstituted phenazinyl group, a substituted or unsubstituted phenothiazinyl group, a substituted or unsubstituted phenoxazinyl group, a substituted or unsubstituted carbazolyl group, a substituted or unsubstituted dibenzofuranyl group, or a substituted or unsubstituted dibenzothiophenyl group, or a combination thereof, but is not limited thereto.

In the present specification, hole characteristics refer to an ability to donate an electron to form a hole when an electric field is applied and that a hole formed in the anode may be easily injected into the light emitting layer and transported in the light emitting layer due to conductive characteristics according to the highest occupied molecular orbital (HOMO) level.

In addition, electron characteristics refer to an ability to accept an electron when an electric field is applied and that electron formed in the cathode may be easily injected into the light emitting layer and transported in the light emitting layer due to conductive characteristics according to the lowest unoccupied molecular orbital (LUMO) level.

Hereinafter, a compound according to an embodiment is described.

A compound according an embodiment is represented by Chemical Formula 1.

[Chemical Formula 1]

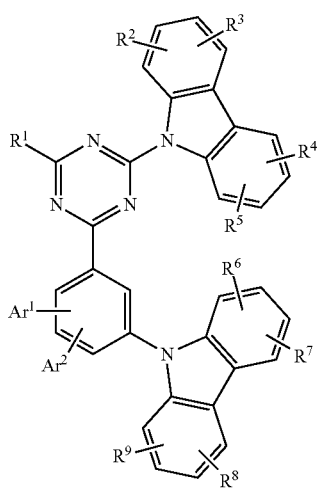

In Chemical Formula 1,
$R^1$ is a C6 to C20 aryl group that is substituted or unsubstituted with a C1 to C5 alkyl group or C6 to C12 aryl group, a substituted or unsubstituted dibenzofuranyl group that is substituted or unsubstituted with a C6 to C12 aryl group, or a dibenzothiophenyl group that is substituted or unsubstituted with a C6 to C12 aryl group, $R^2$ to $R^9$ are each independently hydrogen, deuterium, a cyano group, a halogen, a substituted or unsubstituted amine group, a substituted or unsubstituted C1 to C30 alkyl group, a substituted or unsubstituted C6 to C30 aryl group, a substituted or unsubstituted C2 to C30 heterocyclic group, or a combination thereof, and $Ar^1$ and $Ar^2$ are each independently hydrogen, deuterium, or a C6 to C20 aryl group.

The compound represented by Chemical Formula 1 may have a structure that one carbazole group is directly linked to triazine without a linking group in an N-direction, while another carbazole group also is linked to the triazine through meta-phenylene in the N-direction in the center of the triazine.

Since one carbazole group is directly linked to the triazine in the N-direction, that is, at a 9-position, without a linking group, the compound has a relatively deep LUMO energy level, which is advantageous for electron injection and transportation.

In addition, since another carbazole group is linked to the triazine in the N-direction, that is, the 9-position and thus breaks a π-bond through a C—N bond, an electron cloud between HOMO-LUMO is clearly localized into a hole transport moiety and an electron transport moiety, and this localization is more effectively separated by linking the carbazole group to the triazine through meta-phenylene, maximizing a life-span improvement effect.

In other words, in a device including the compound represented by Chemical Formula 1, since the advantageous hole/electron injection and transportation and the effective localization of the electron cloud realize a stable structure for electrons and holes, more advantageous characteristics for a life-span may be obtained.

In particular, the compound includes the triazine as the center core to secure fast electron injection and mobility and thus to achieve a charge balance with carbazole moieties having strong hole mobility and also greatly contributes to long life-span characteristics.

For example, $R^1$ may be a phenyl group that is unsubstituted or substituted with a C6 to C12 aryl group, a biphenyl group that is unsubstituted or substituted with a C6 to C12 aryl group, a fluorenyl group that is unsubstituted or substituted with a C6 to C12 aryl group, a dibenzofuranyl group that is unsubstituted or substituted with a C6 to C12 aryl group or a dibenzothiophenyl group that is unsubstituted or substituted with a C6 to C12 aryl group.

For example, $R^1$ may be selected from the substituents of Group I.

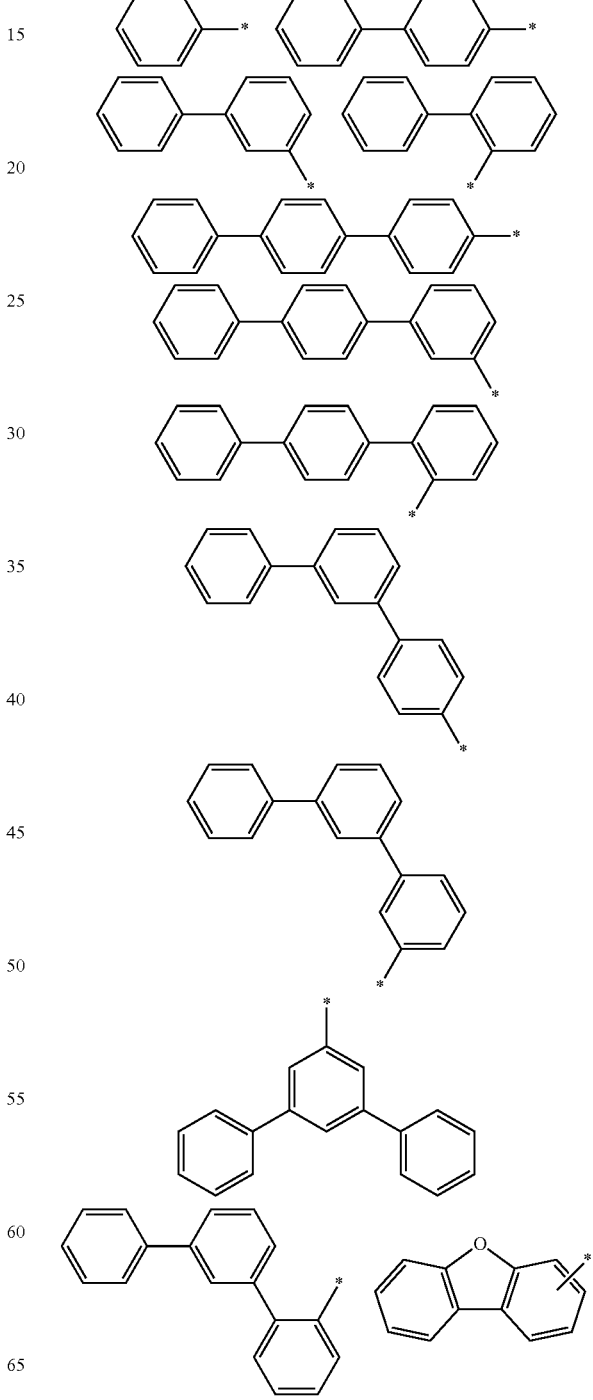

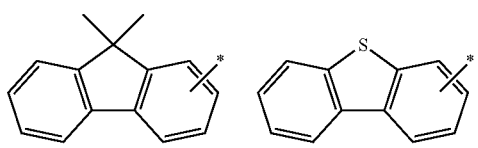

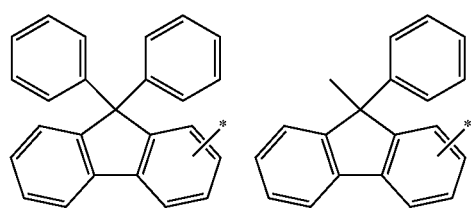

For example, $R^2$ to $R^5$ may each independently be hydrogen or a C6 to C12 aryl group, $R^6$ to $R^9$ may each independently be hydrogen or a C6 to C12 aryl group.

As a specific example, all of $R^2$ to $R^5$ may be hydrogen or any one of $R^2$ to $R^5$ may be a phenyl group, and all of $R^6$ to $R^9$ may be hydrogen or any one of $R^6$ to $R^9$ may be a phenyl group.

For example, $Ar^1$ and $Ar^2$ may each independently be hydrogen or a C6 to C12 aryl group.

As a specific example, $Ar^1$ and $Ar^2$ may each independently be hydrogen, a phenyl group, or a biphenyl group.

For example, $Ar^1$ and $Ar^2$ may be each hydrogen.

In the most specific embodiment, the compound for an organic optoelectronic device represented by Chemical Formula 1 may be one selected from compounds of Group 1, but is not limited thereto.

[Group 1]

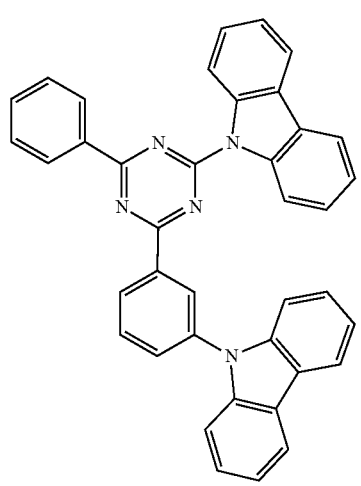

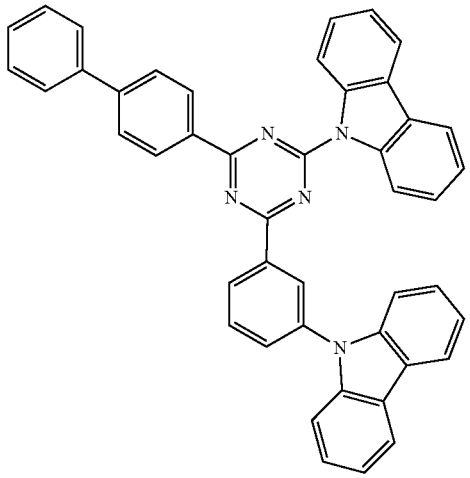

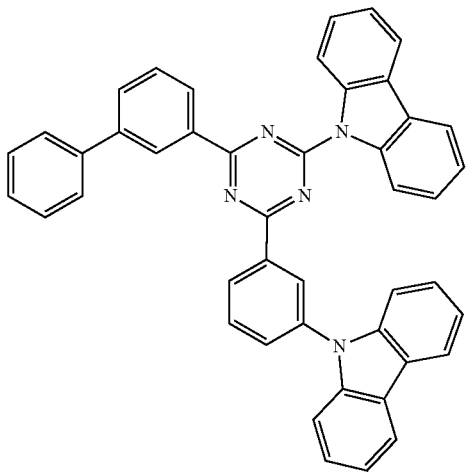

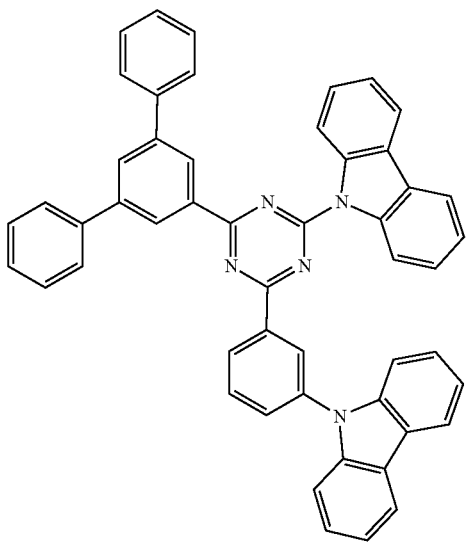

5
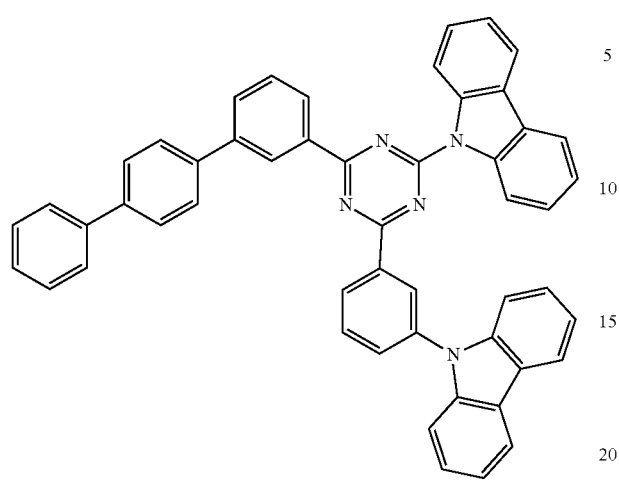
6
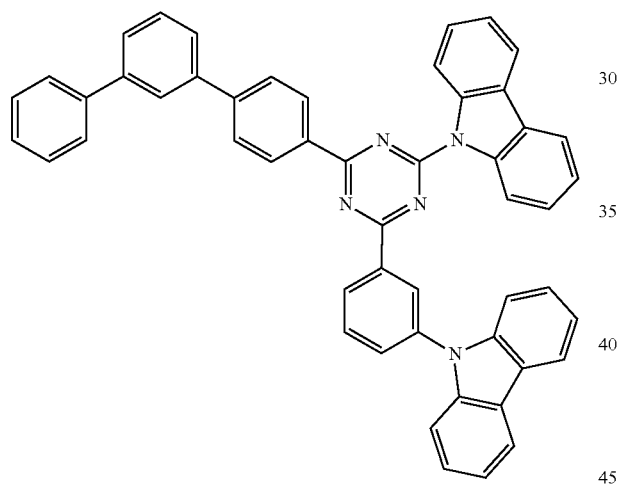
7
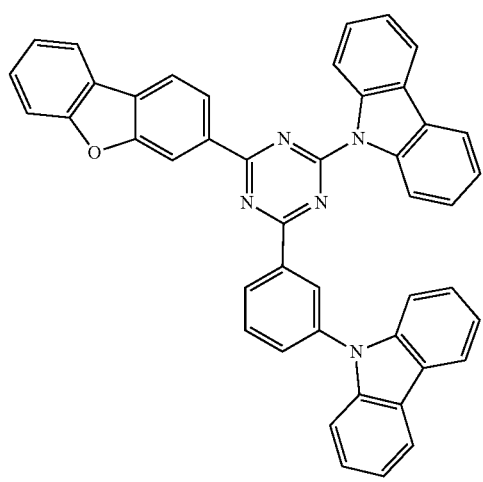
8
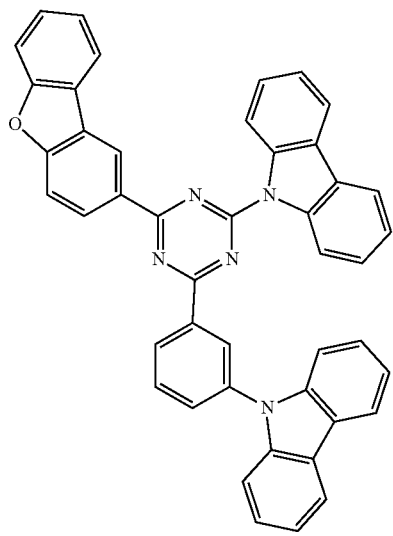
9
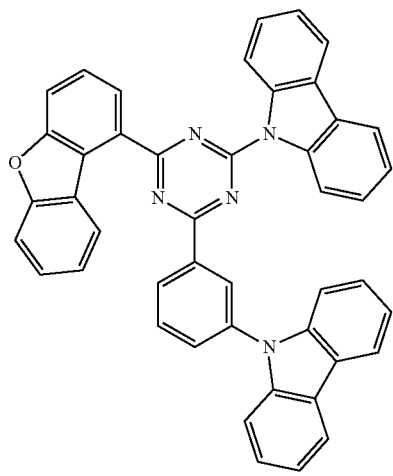
10
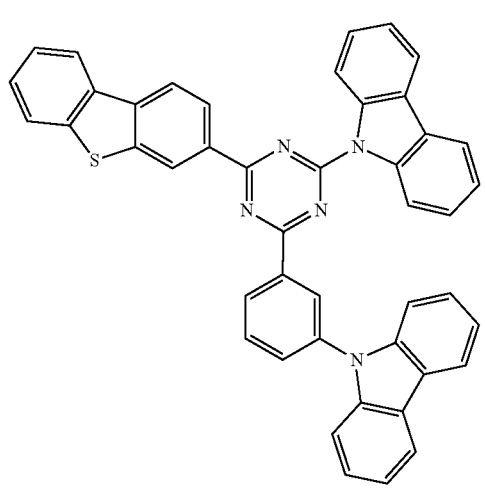

11
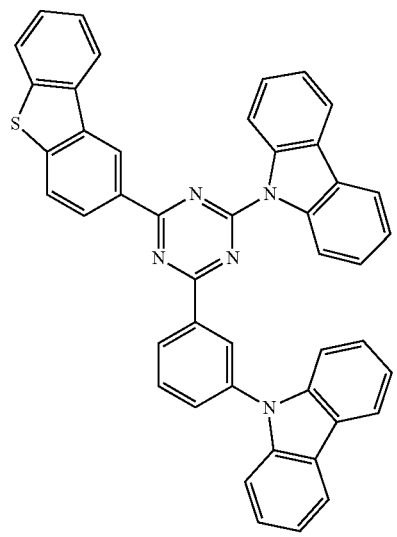
12
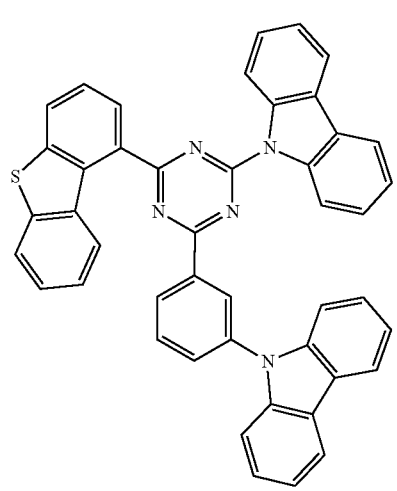
13
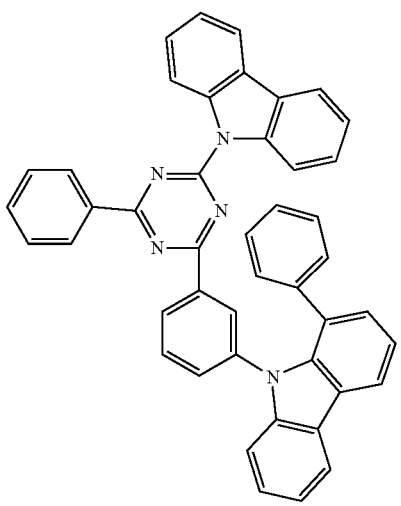
14
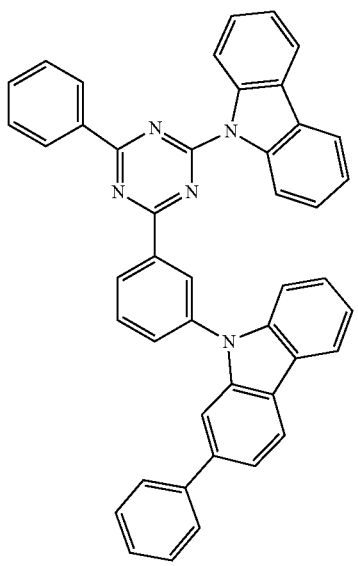
15
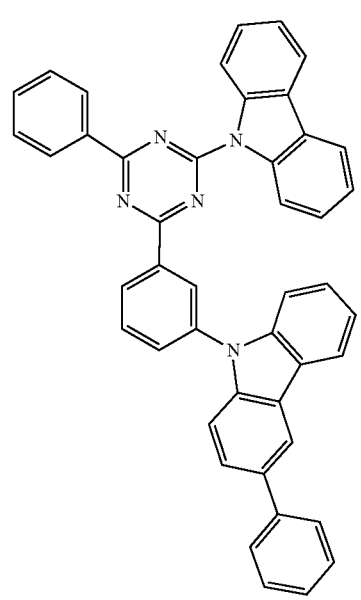
16
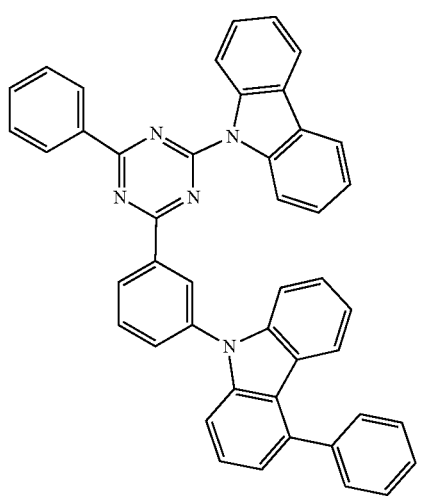

17
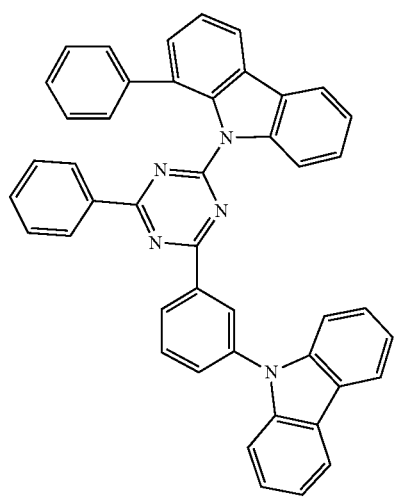
18
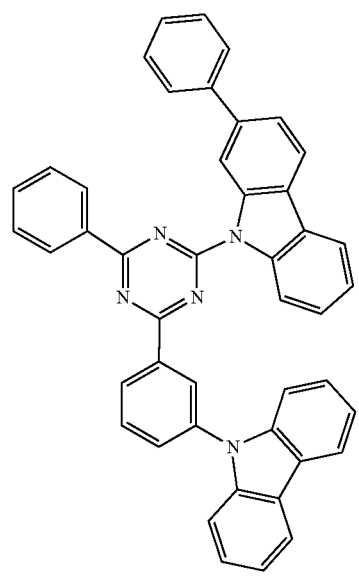
19
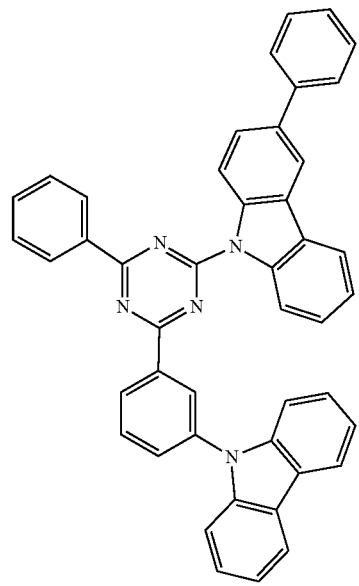
20
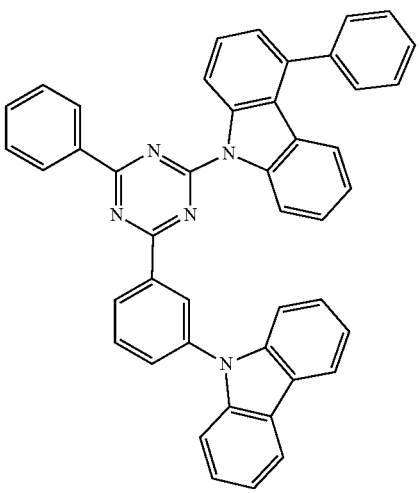
21
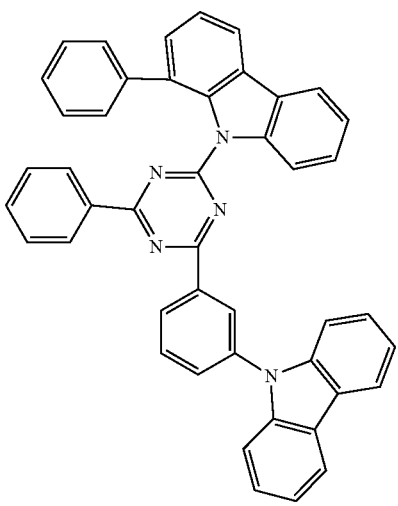
22
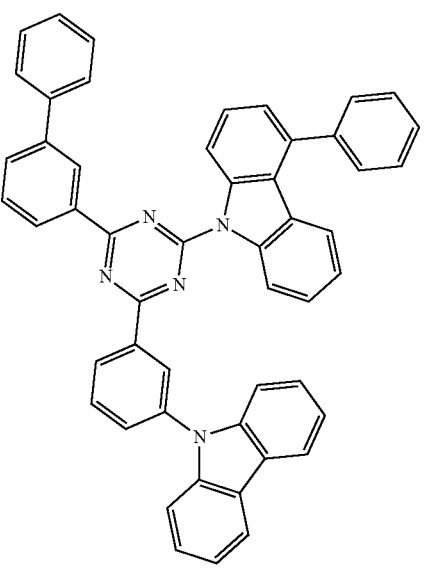

23
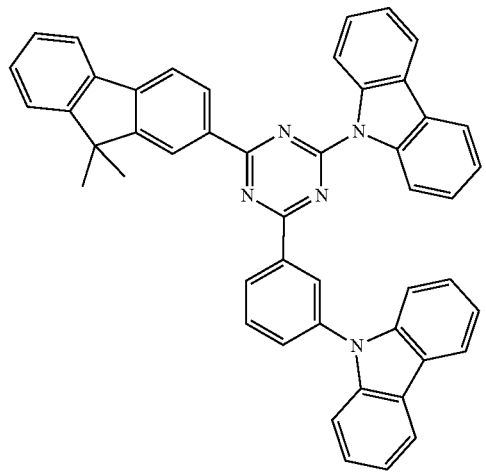

24
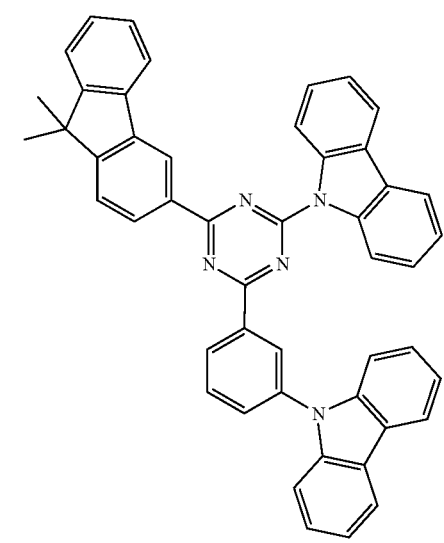

25
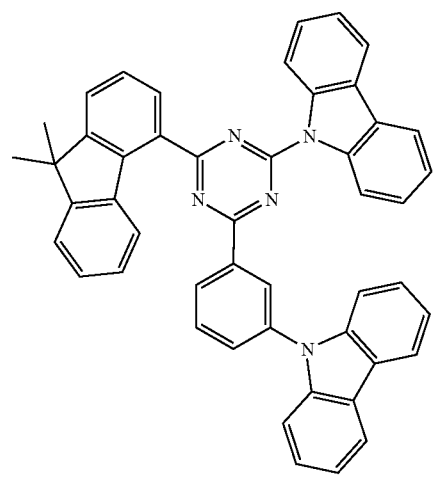

26
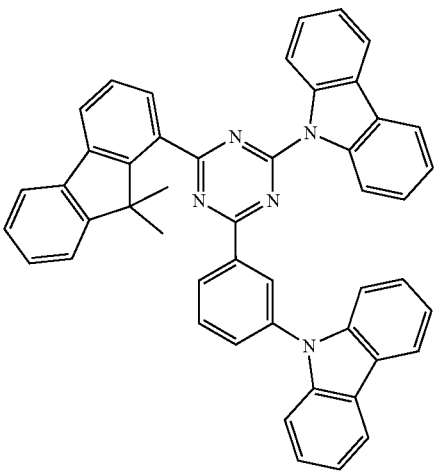

27
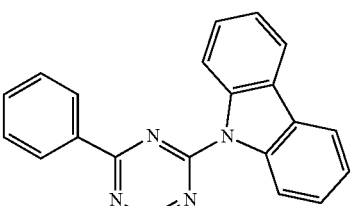
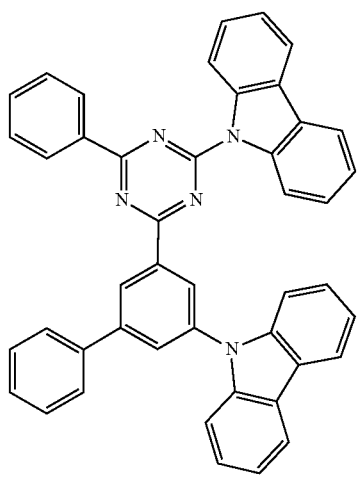

28
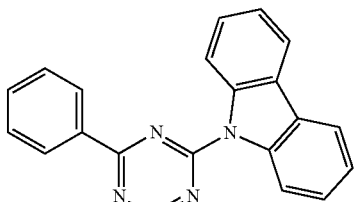
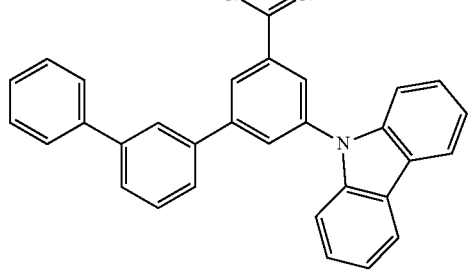

In addition to the aforementioned compound for an organic optoelectronic device, one or more compounds may be further included.

For example, a dopant may be further included.

The dopant may be a phosphorescent dopant, for example, a red or green phosphorescent dopant, and may be, for example, a green phosphorescent dopant.

The dopant is a material mixed with the composition including the compound for an organic optoelectronic device in a small amount to cause light emission, and may be generally a material such as a metal complex that emits light by multiple excitation into a triplet or more. The dopant may be, for example an inorganic, organic, or organic/inorganic compound, and one or more types thereof may be used.

An example of the dopant may be a phosphorescent dopant, and examples of the phosphorescent dopant may include organometallic compounds including Ir, Pt, Os, Ti, Zr, Hf, Eu, Tb, Tm, Fe, Co, Ni, Ru, Rh, Pd, or a combination thereof. The phosphorescent dopant may be, for example, a compound represented by Chemical Formula Z, but is not limited thereto.

$$L^5MX^a$$ [Chemical Formula Z]

In Chemical Formula Z, M is a metal, and $L^5$ and $X^a$ are the same or different from each other and are ligands forming a complex compound with M.

The M may be, for example, Ir, Pt, Os, Ti, Zr, Hf, Eu, Tb, Tm, Fe, Co, Ni, Ru, Rh, Pd, or a combination thereof, and $L^5$ and $X^a$ may be, for example, a bidentate ligand.

The aforementioned compound for an organic optoelectronic device or composition for an organic optoelectronic device may be used in a dry film formation method such as chemical vapor deposition (CVD).

Hereinafter, an organic optoelectronic device including the aforementioned compound for an organic optoelectronic device is described.

The organic optoelectronic device may be any device to convert electrical energy into photoenergy and vice versa without particular limitation, and may be, for example an organic photoelectric device, an organic light emitting diode, an organic solar cell, and an organic photoconductor drum.

Herein, an organic light emitting diode as one example of an organic optoelectronic device is described referring to drawings.

FIGS. 1 and 2 are cross-sectional views illustrating organic light emitting diodes according to an embodiment.

Referring to FIG. 1, an organic light emitting diode 100 according to an embodiment includes an anode 120 and a cathode 110 facing each other and an organic layer 105 disposed between the anode 120 and cathode 110.

The anode 120 may be made of a conductor having a large work function to help hole injection, and may be for example a metal, a metal oxide and/or a conductive polymer. The anode 120 may be, for example a metal such as nickel, platinum, vanadium, chromium, copper, zinc, gold, and the like or an alloy thereof; a metal oxide such as zinc oxide, indium oxide, indium tin oxide (ITO), indium zinc oxide (IZO), and the like; a combination of a metal and an oxide such as ZnO and Al or $SnO_2$ and Sb; a conductive polymer such as poly(3-methylthiophene), poly(3,4-(ethylene-1,2-dioxy)thiophene) (PEDT), polypyrrole, and polyaniline, but is not limited thereto.

The cathode 110 may be made of a conductor having a small work function to help electron injection, and may be for example a metal, a metal oxide and/or a conductive polymer. The cathode 110 may be for example a metal such as magnesium, calcium, sodium, potassium, titanium, indium, yttrium, lithium, gadolinium, aluminum silver, tin, lead, cesium, barium, and the like, or an alloy thereof; a multi-layer structure material such as LiF/Al, $LiO_2$/Al, LiF/Ca, LiF/Al, and $BaF_2$/Ca, but is not limited thereto.

The organic layer 105 may include the aforementioned compound for an organic optoelectronic device.

The organic layer 105 may include the light emitting layer 130, and the light emitting layer 130 may include the aforementioned compound for an organic optoelectronic device.

The composition for an organic optoelectronic device further including a dopant may be, for example, a green light emitting composition.

The light emitting layer 130 may include, for example, the aforementioned compound for an organic optoelectronic device as a phosphorescent host.

The organic layer may further include an auxiliary layer in addition to the light emitting layer.

The auxiliary layer may be, for example, a hole auxiliary layer 140.

Referring to FIG. 2, the organic light emitting diode 200 further includes a hole auxiliary layer 140 in addition to the light emitting layer 130. The hole auxiliary layer 140 may further increase hole injection and/or hole mobility and block electrons between the anode 120 and the light emitting layer 130.

The hole auxiliary layer 140 may include, for example, at least one of the compounds of Group D.

Specifically, the hole auxiliary layer 140 may include a hole transport layer between the anode 120 and the light emitting layer 130, and a hole transport auxiliary layer between the light emitting layer 130 and the hole transport layer. At least one of the compounds of Group D may be included in the hole transport auxiliary layer.

[Group D]

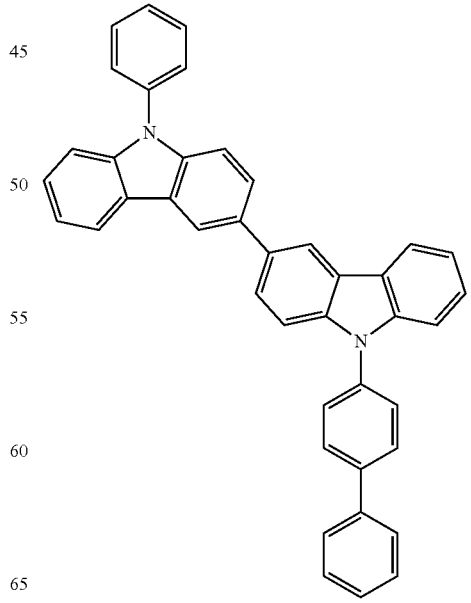

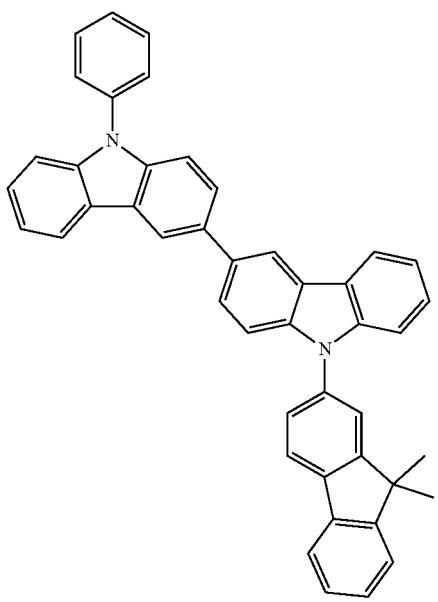
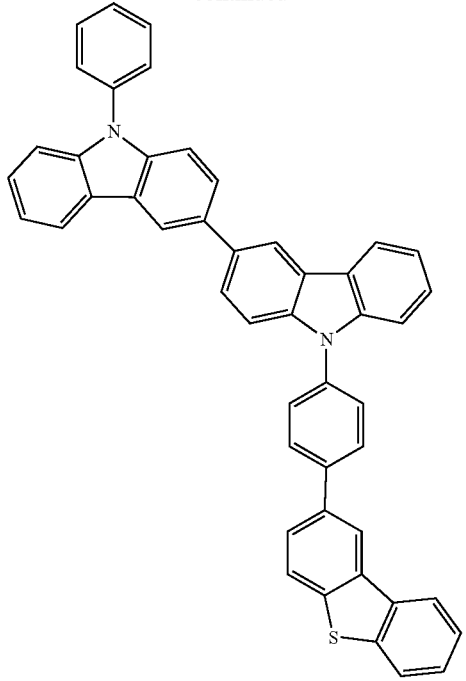
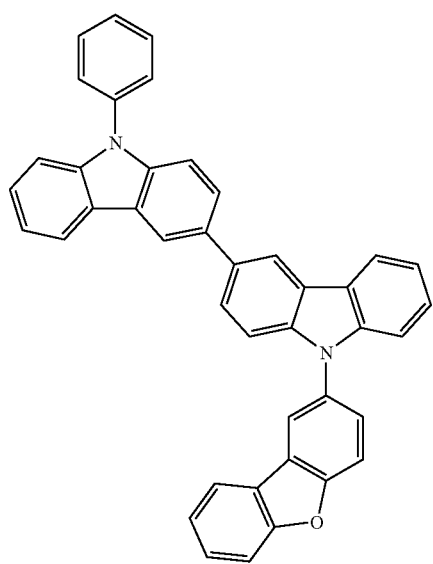
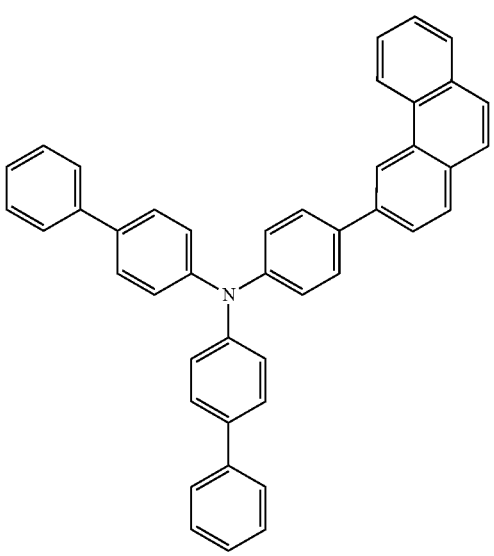

-continued
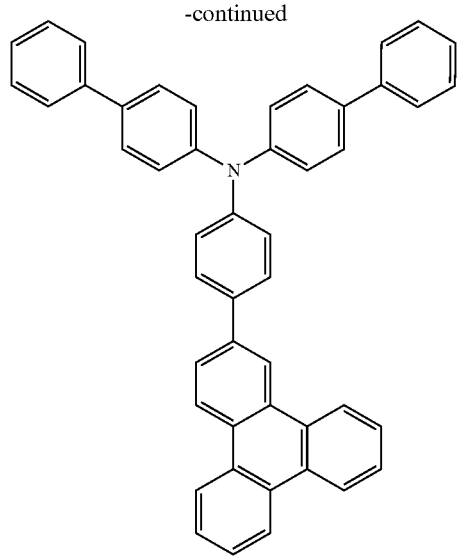
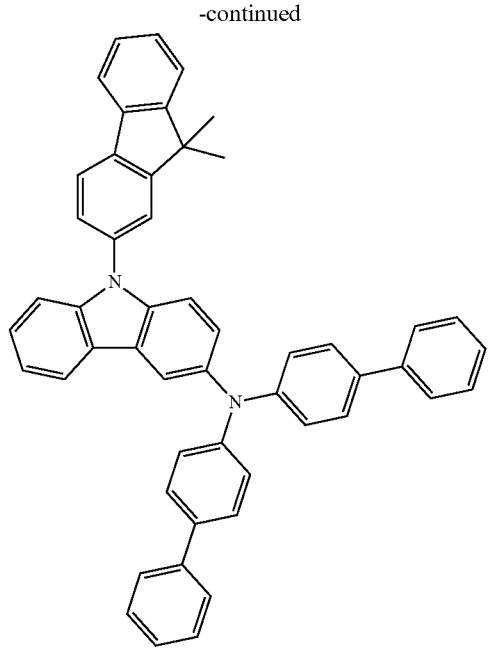
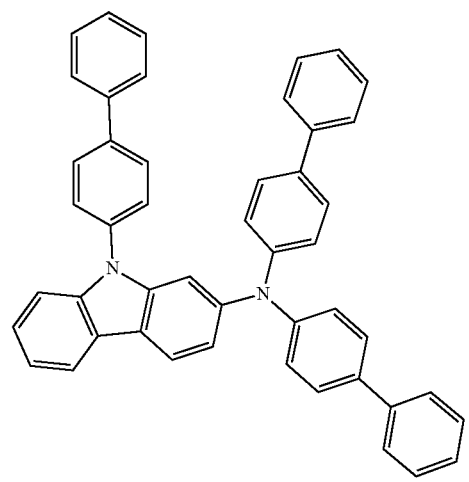
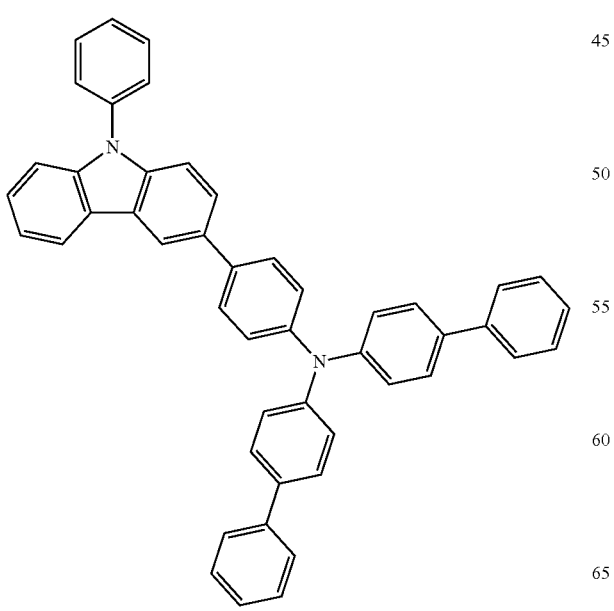
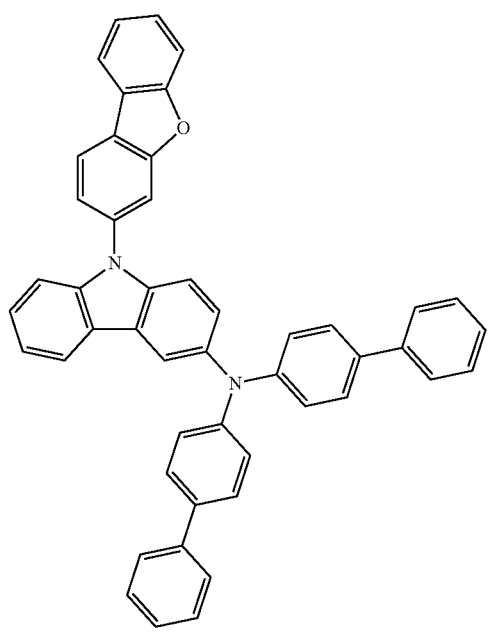

23
-continued
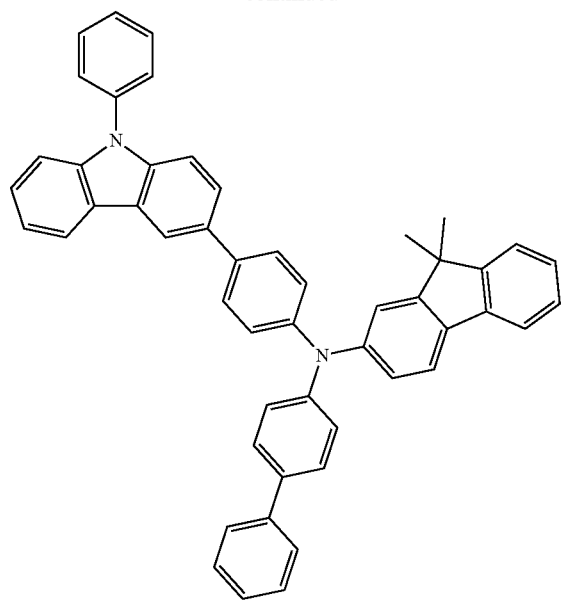
24
-continued
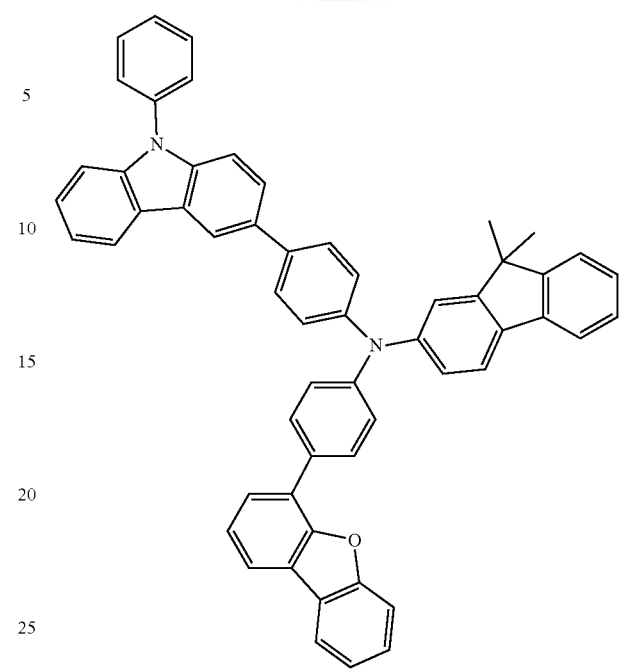
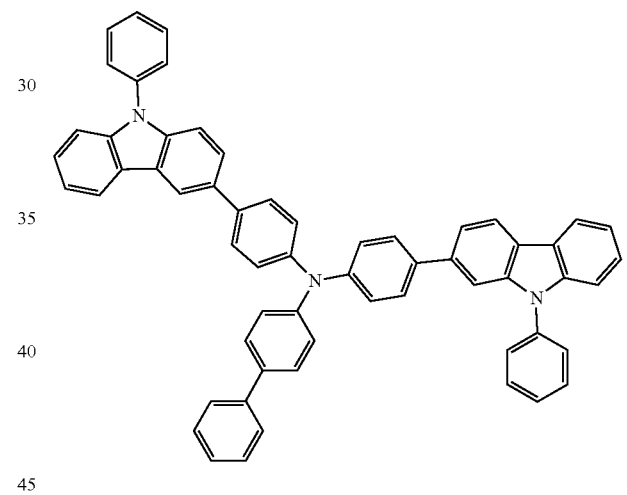
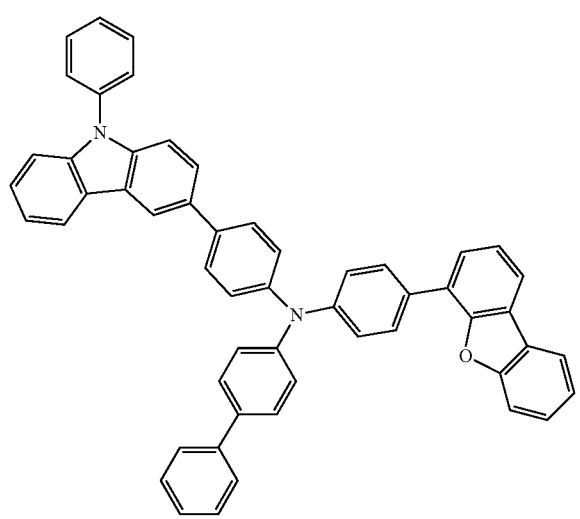
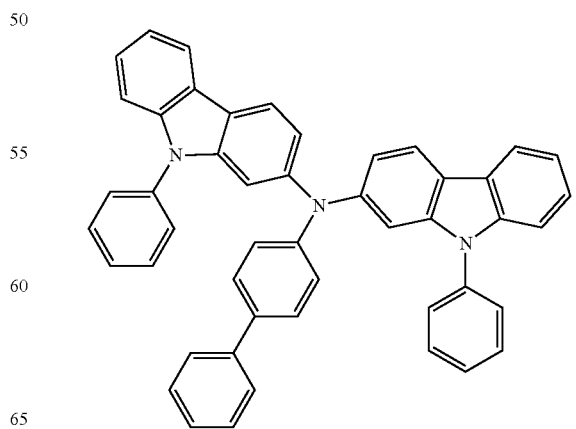

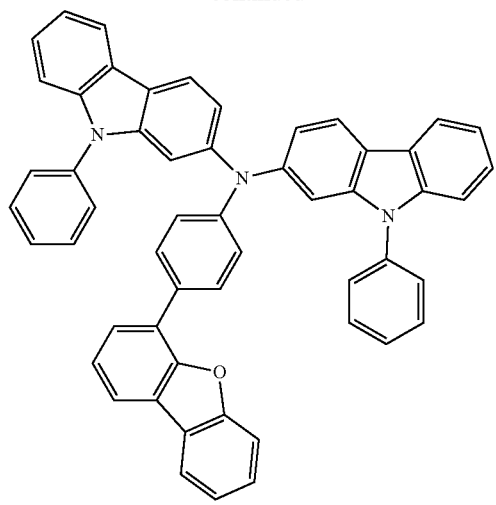
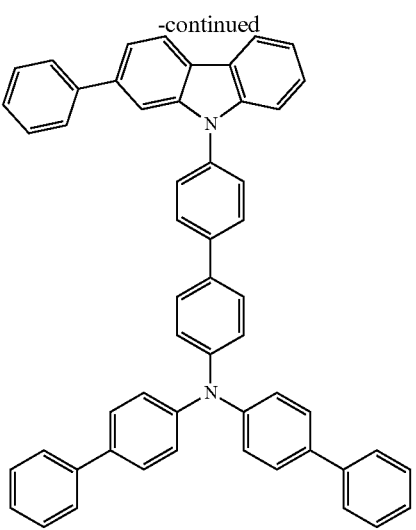
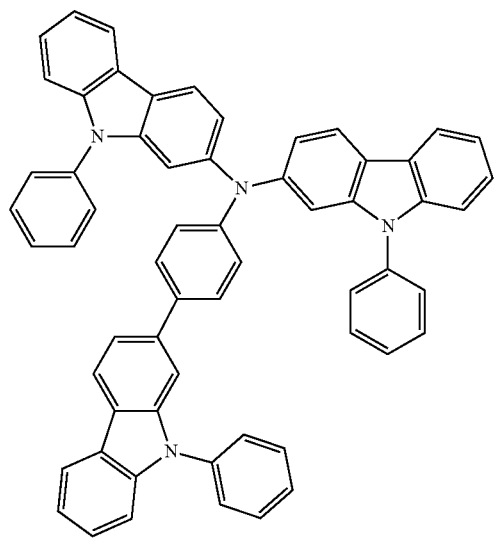
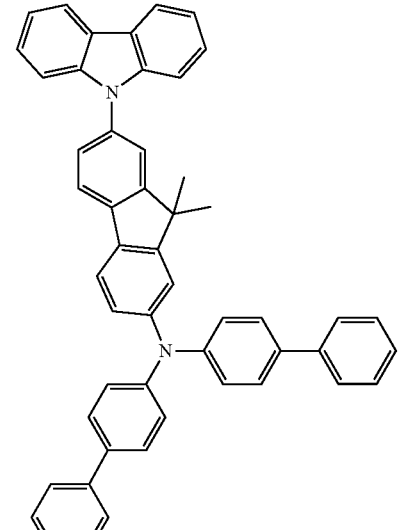
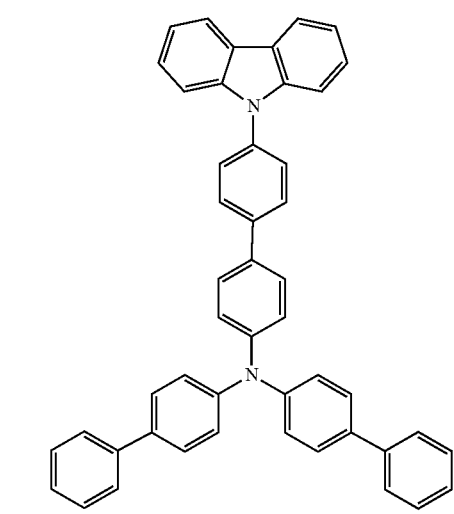
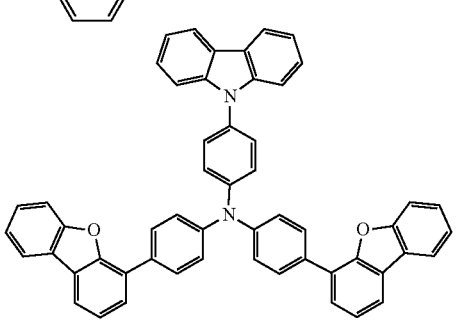
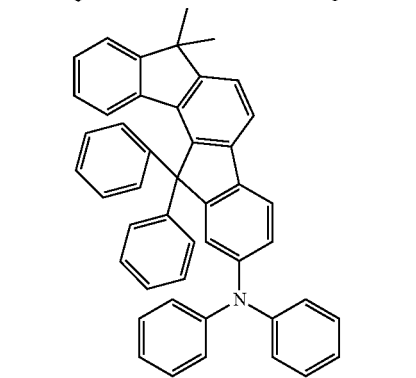

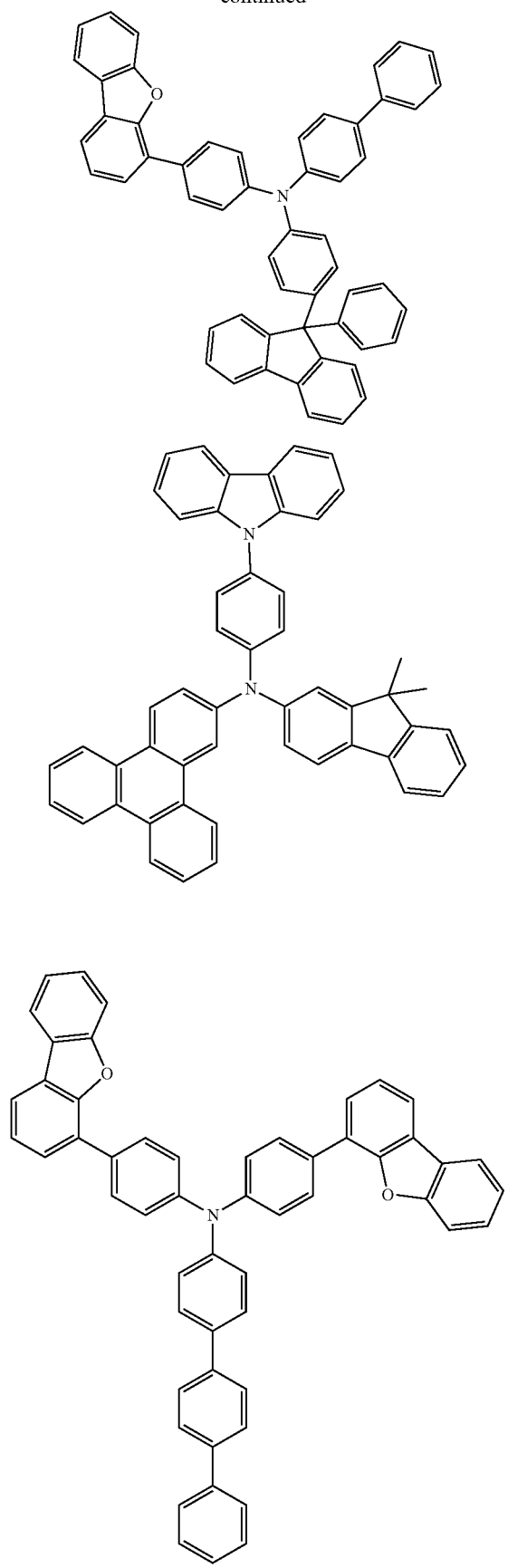
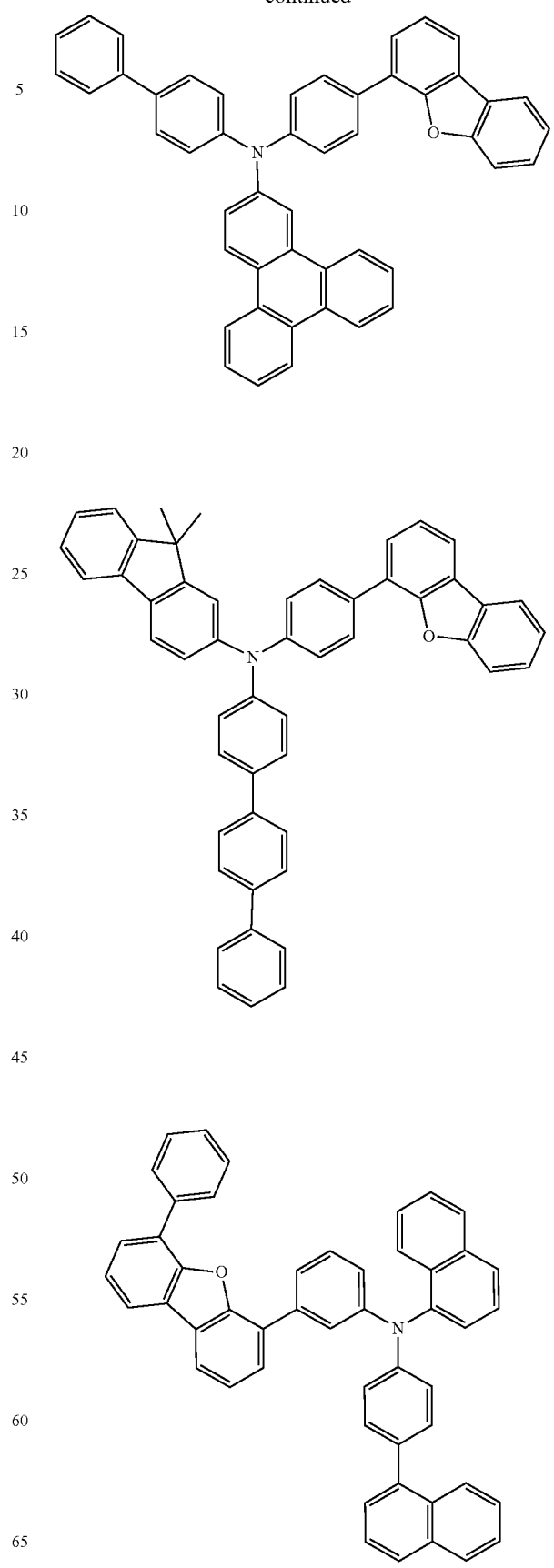

29
-continued
30
-continued
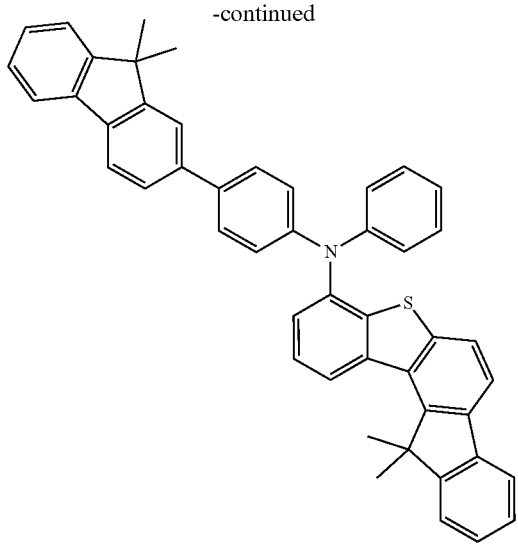
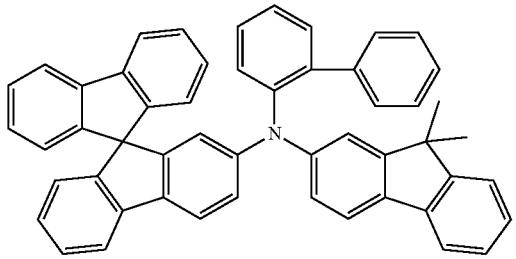
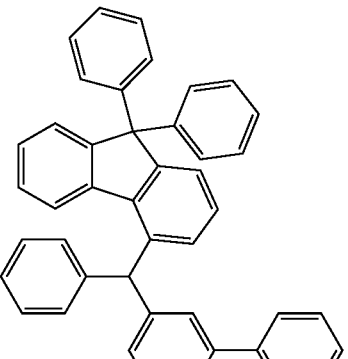
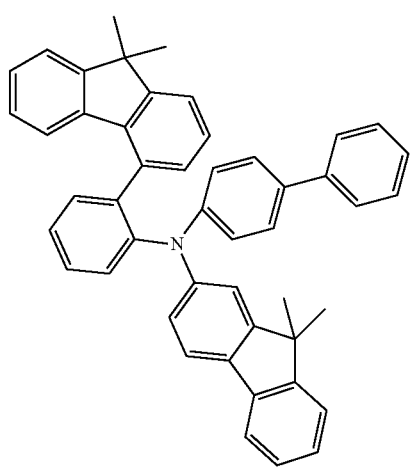
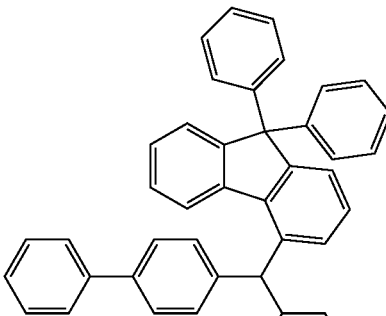
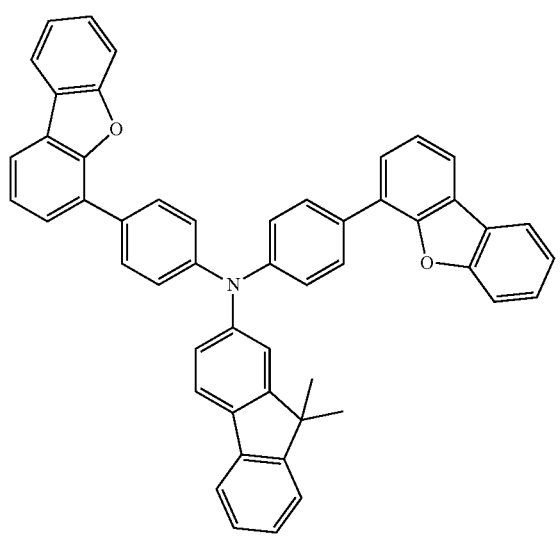
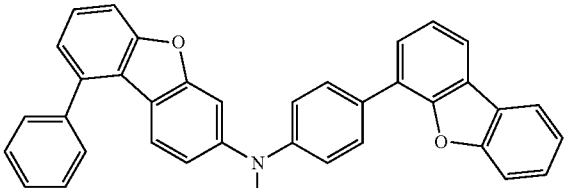
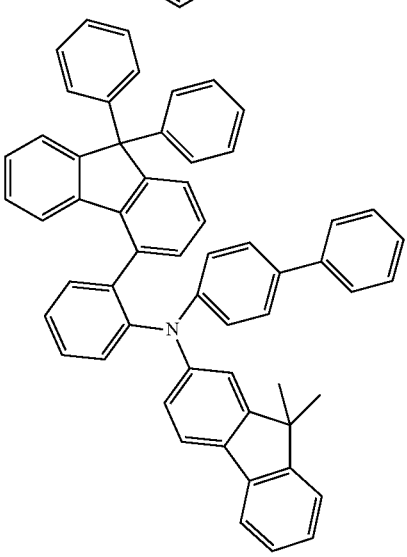

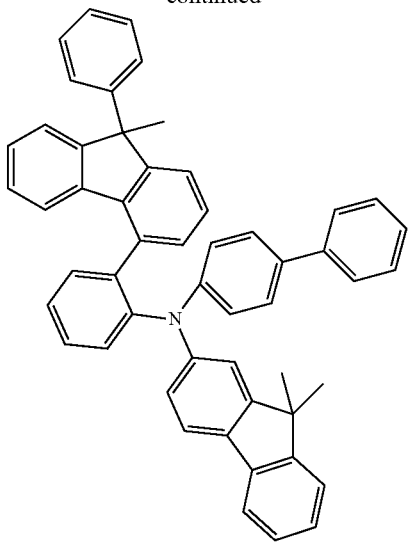
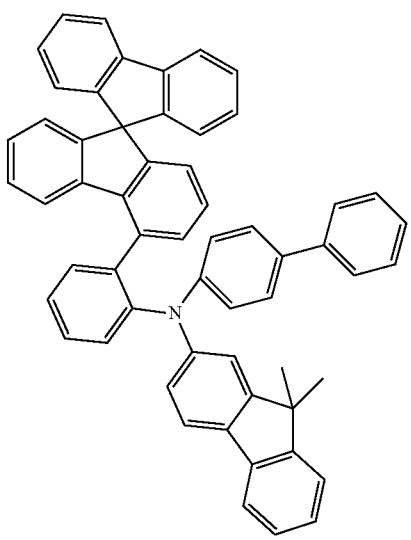
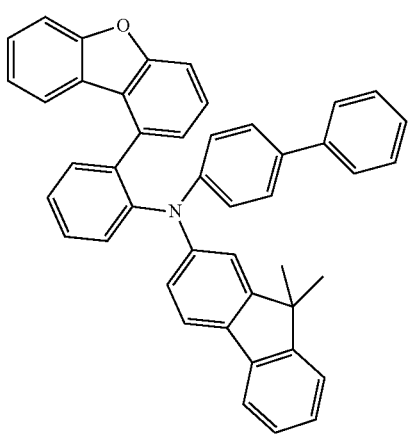
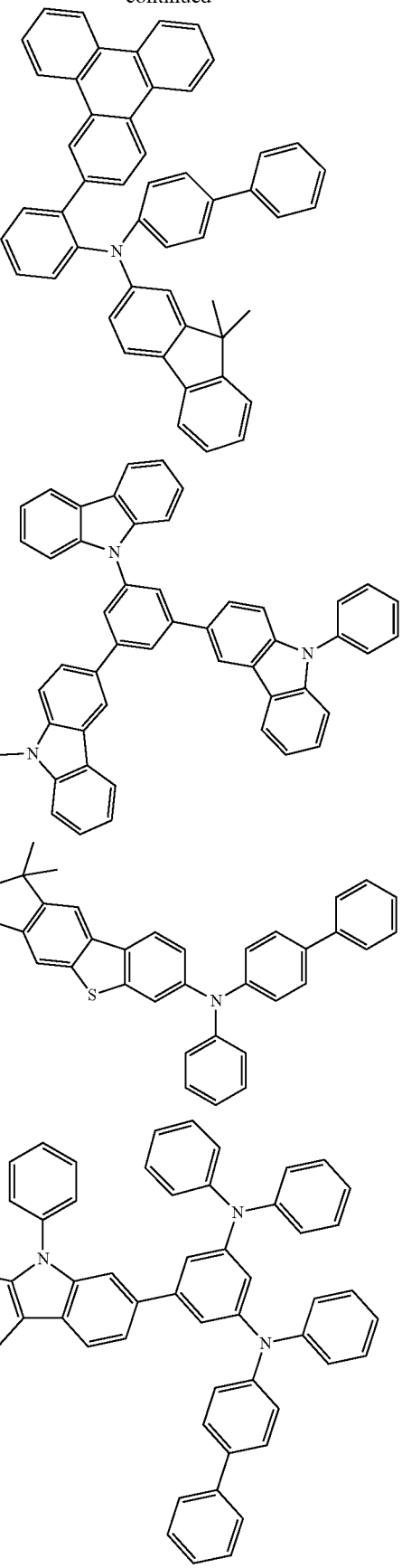

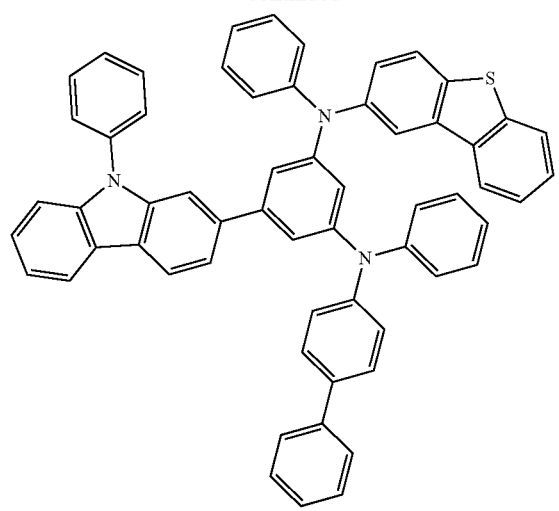
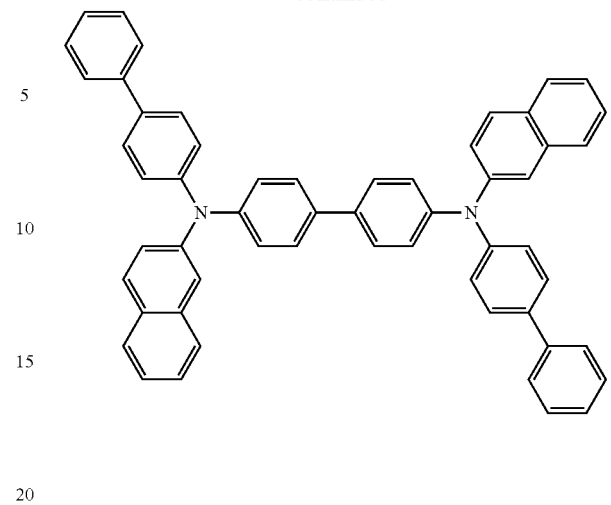
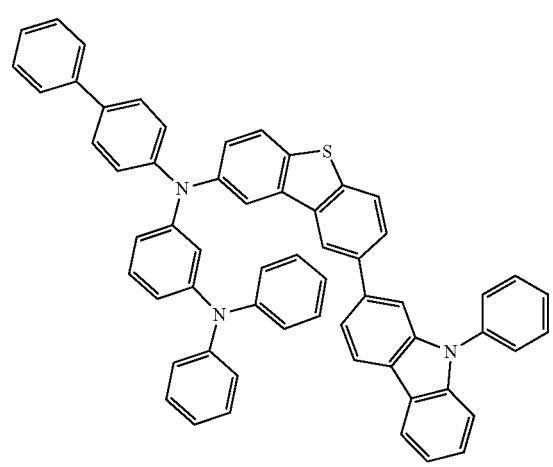
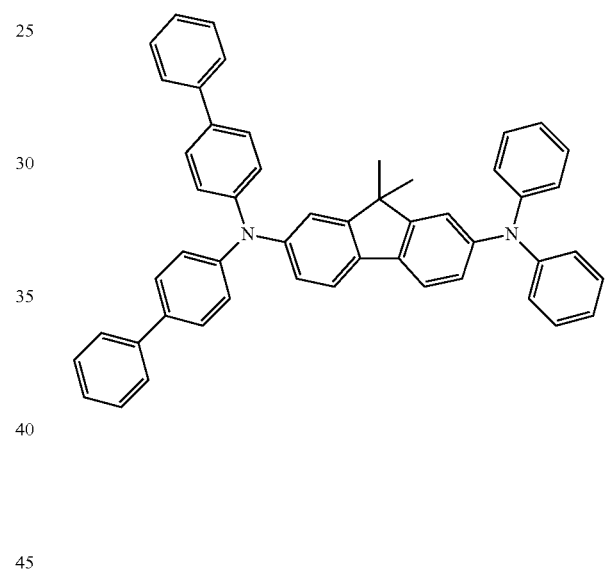
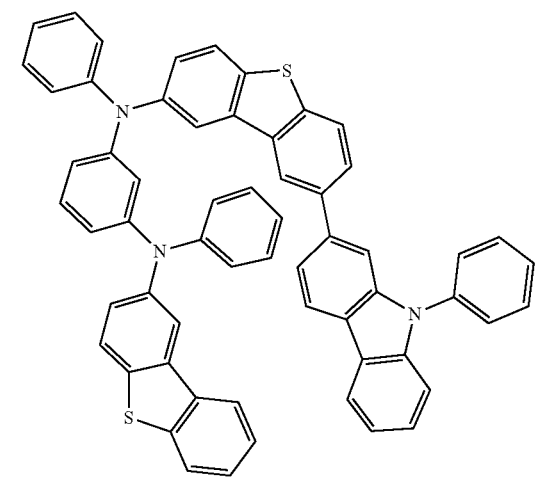
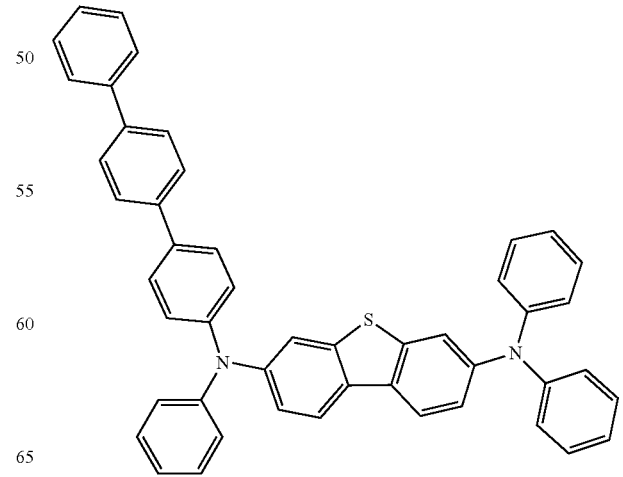

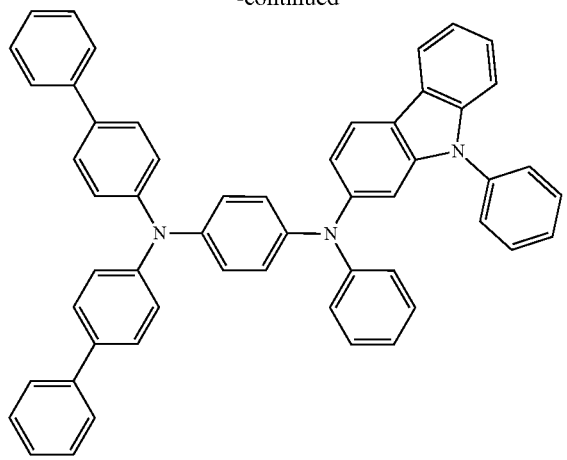
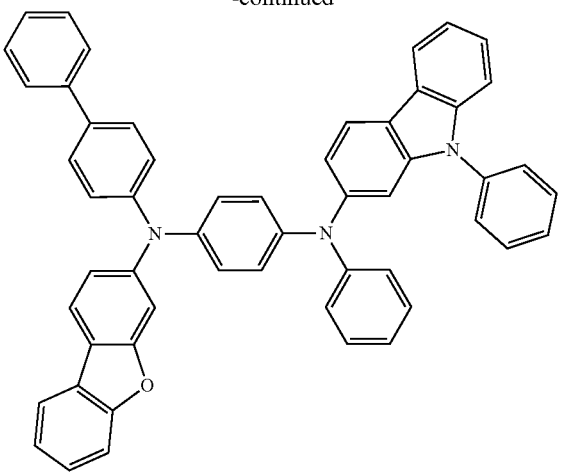

37
-continued
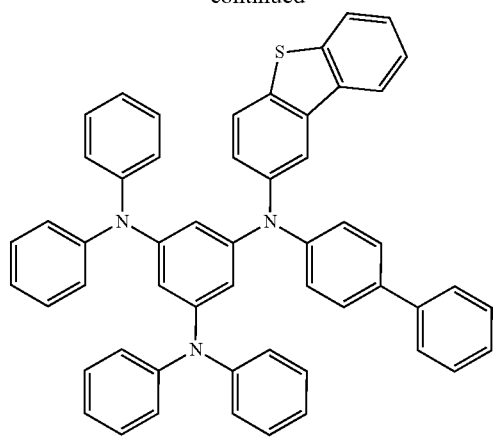
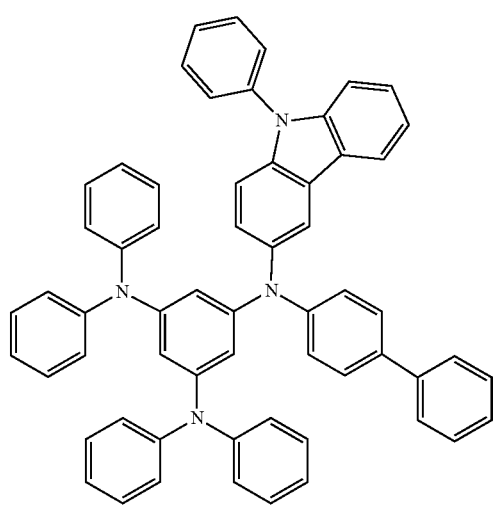
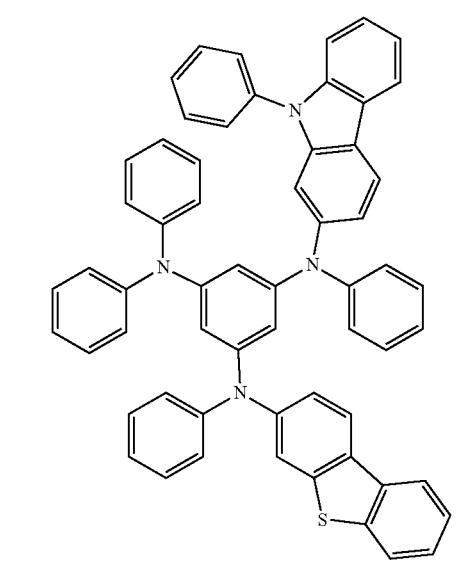
38
-continued
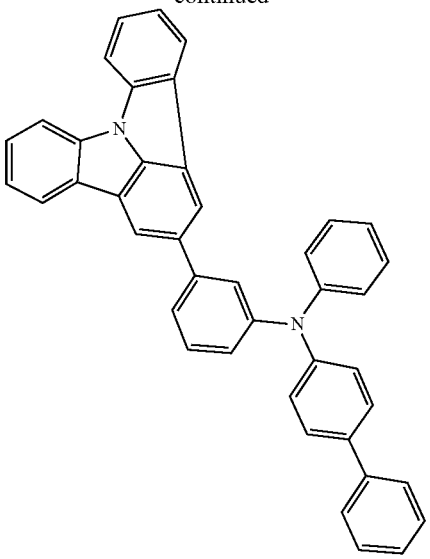
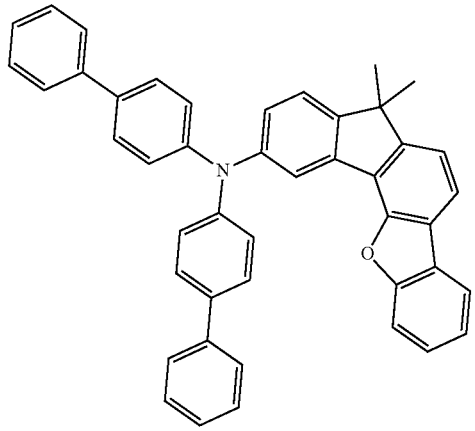
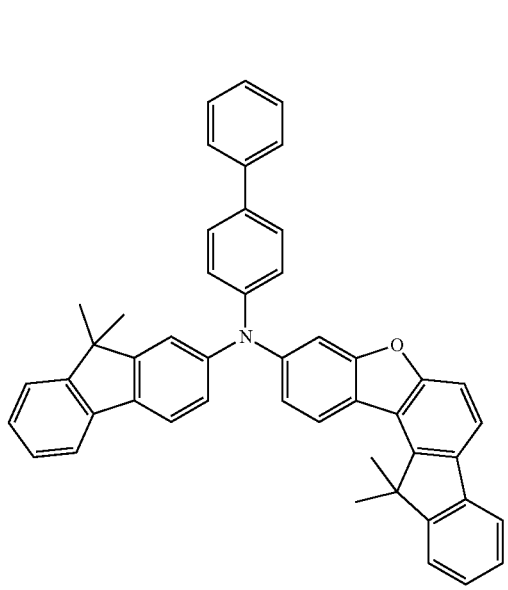

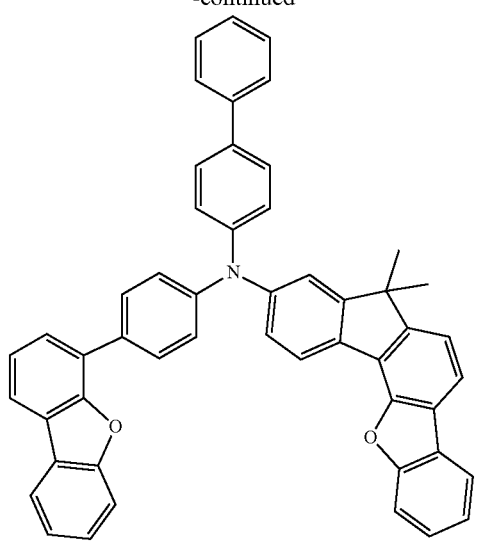
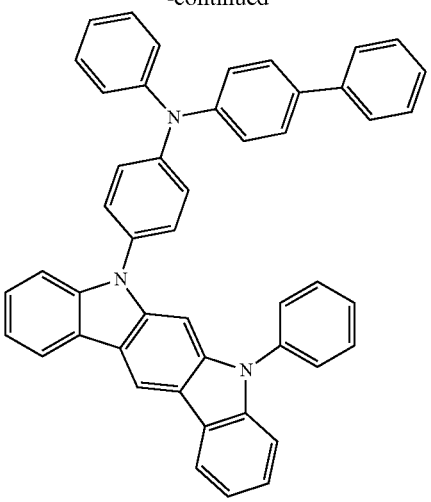
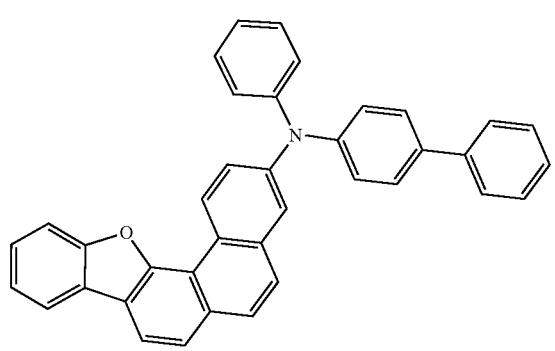
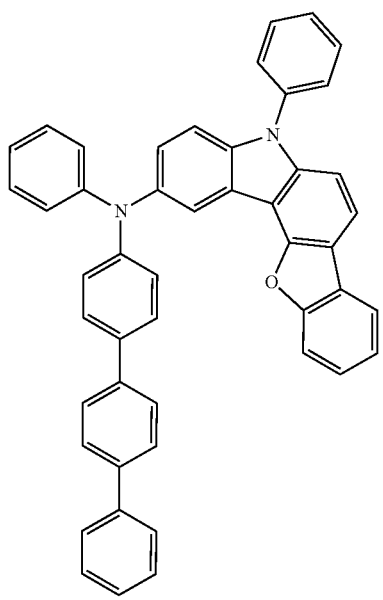
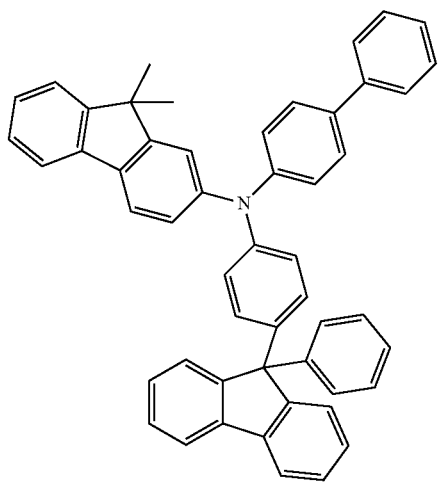
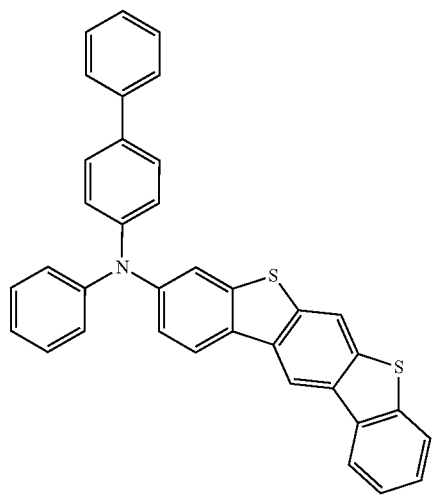

-continued

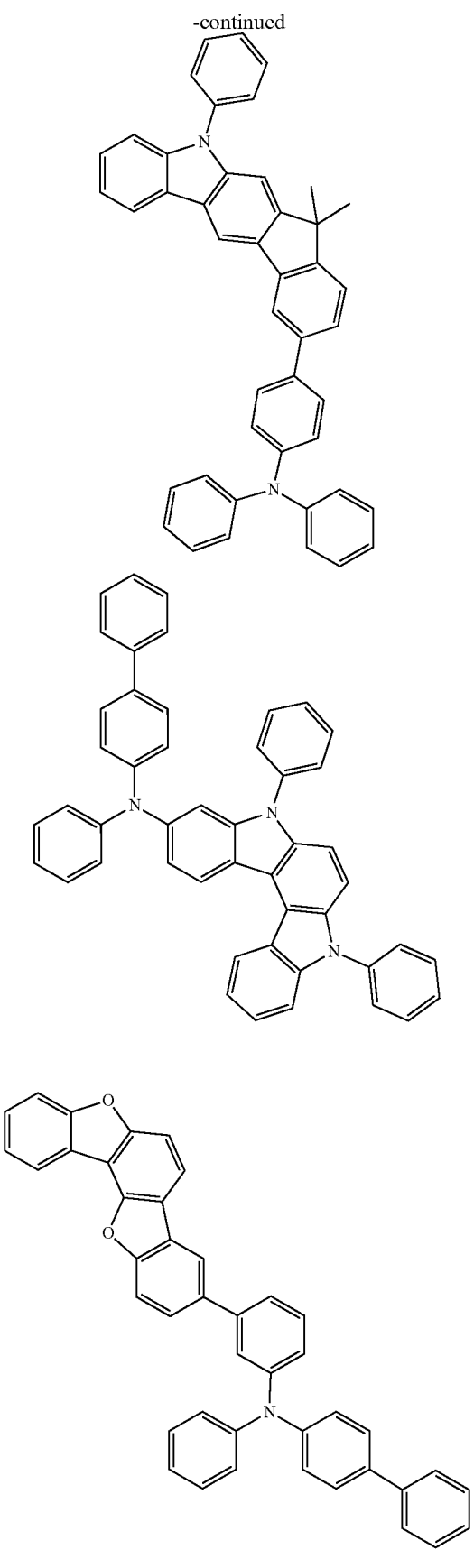

In addition to the aforementioned compounds, known compounds described in U.S. Pat. No. 5,061,569A, JP1993-009471A, WO1995-009147A1, JP1995-126615A, JP1998-095973A, and the like, and compounds having similar structures may be used for the hole transport auxiliary layer.

In addition, in an embodiment of the present invention, the organic light emitting diode may further include an electron transport layer, an electron injection layer, and a hole injection layer as the organic layer 105 in FIG. 1 or 2.

The organic light emitting diodes 100 and 200 may be manufactured by forming an anode or a cathode on a substrate, forming an organic layer by a dry film method such as evaporation, sputtering, plasma plating, and ion plating, and forming a cathode or an anode thereon.

The organic light emitting diode may be applied to an organic light emitting display device.

Hereinafter, the embodiments are illustrated in more detail with reference to examples. However, these examples are exemplary, and the present scope is not limited thereto.

Hereinafter, starting materials and reactants used in Examples and Synthesis Examples were purchased from Sigma-Aldrich Co. Ltd., TCI Inc., Tokyo chemical industry or P&H tech as far as there is no particular comment or were synthesized by known methods.

(Preparation of Compound for Organic Optoelectronic Device)

The compounds as more specific examples of the compounds of the present invention were synthesized through the following steps.

(Preparation of First Compound for Organic Optoelectronic Device)

Synthesis Example 1: Synthesis of Compound 2

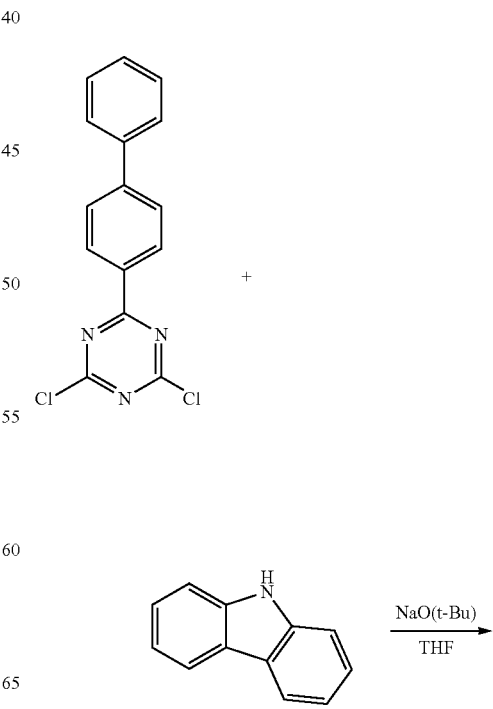

-continued

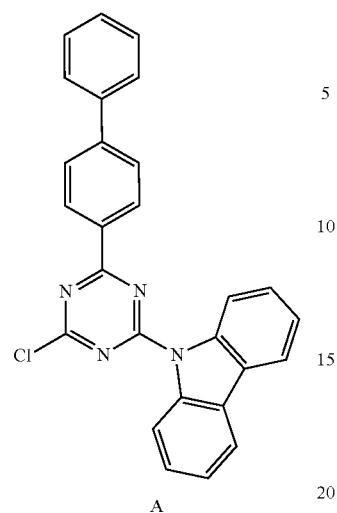

A

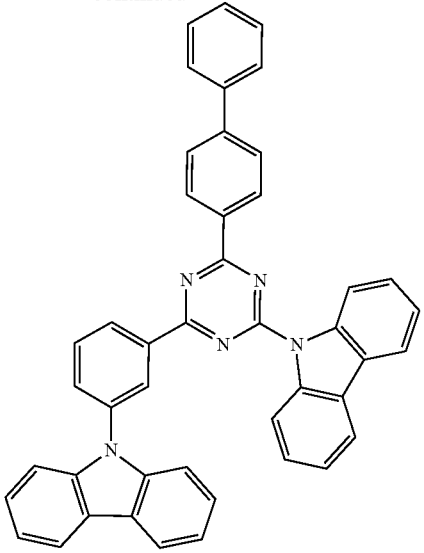

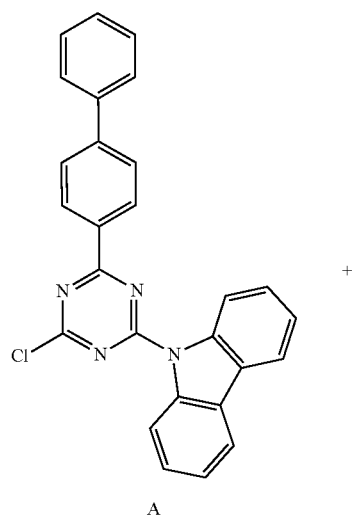

A

+

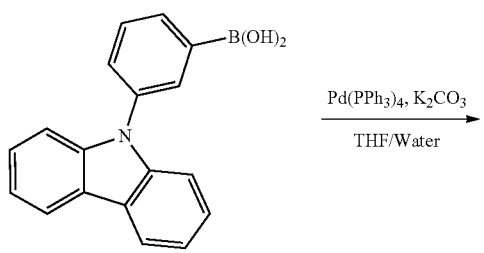

Pd(PPh₃)₄, K₂CO₃
―――――――――→
THF/Water

1ˢᵗ Step: Synthesis of Intermediate A 65.5 g (216.79 mmol) of 2-[1,1'-biphenyl]-4-yl-4,6-dichloro-1,3,5-triazine and 25 g (149.51 mmol) of carbazole were suspended in 800 ml of THF, and then, 15.09 g (156.99 mmol) of NaO(t-Bu) was slowly added thereto. The obtained mixture was stirred at room temperature for 12 hours, and a solid therein was filtered and washed with distilled water, acetone, hexane in order to obtain 40.15 g (Yield: 62%) of Intermediate A.

2ⁿᵈ Step: Synthesis of Compound 2

10 g (23.10 mmol) of Intermediate A, 8.70 g (23.56 mmol) of 3-(9H-carbazol-9-yl) phenyl boronic acid, 0.8 g (0.69 mmol) of Pd(PPh₃)₄, and 6.39 g (46.2 mmol) of K₂CO₃ were suspended in 100 ml of THF and 50 ml of distilled water and then, refluxed and stirred for 12 hours. When a reaction was completed, the resultant was cooled down to room temperature, and a solid produced therein was filtered and then, washed with distilled water and acetone. Then, the solid was heated and dissolved in 200 ml of dichlorobenzene, filtered using a silica gel, and recrystallized in 150 ml of dichlorobenzene to obtain 11 g (Yield: 74%) of Compound 2.

(LC/MS: theoretical value 639.75, measured value: 640.40)

Synthesis Example 2: Synthesis of Compound 7

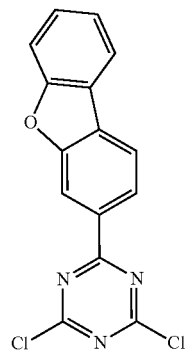

+

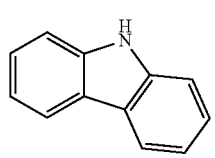

→ (NaOt-Bu, THF)

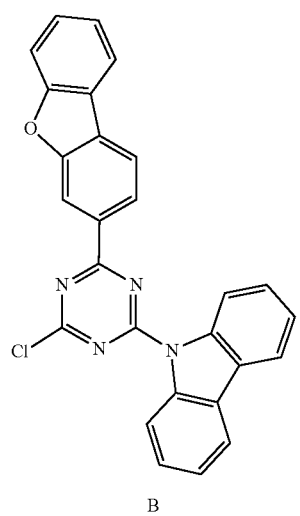

B

1st Step: Synthesis of Intermediate B 15 g (Yield: 54%) of Intermediate B was obtained according to the same method as the 1st step of Synthesis Example 1 except that 30 g (94.89 mmol) of 2,4-dichloro-6-(3-dibenzofuranyl)-1,3,5-triazine was used.

2nd Step: Synthesis of Compound 7

10 g (Yield: 68.4%) of Compound 7 was obtained according to the same method as the 2nd step of Synthesis Example 1 except that 10 g (22.38 mmol) of Intermediate B was added thereto.

(LC/MS: theoretical value 653.73, found: 654.60)

Synthesis Example 3: Synthesis of Comparative Compound R1

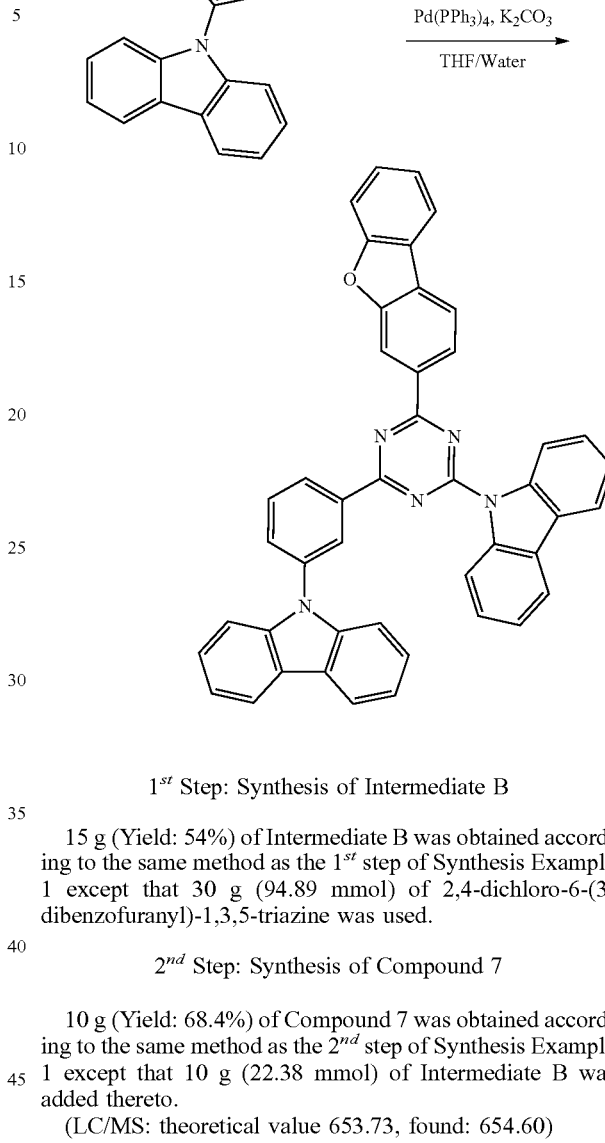

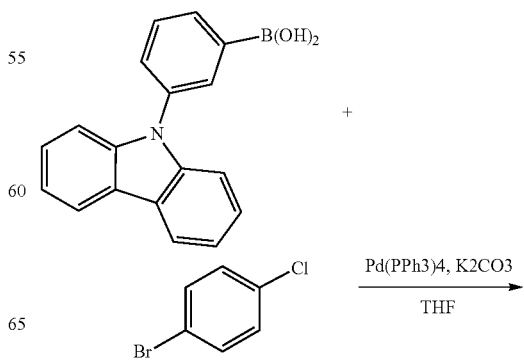

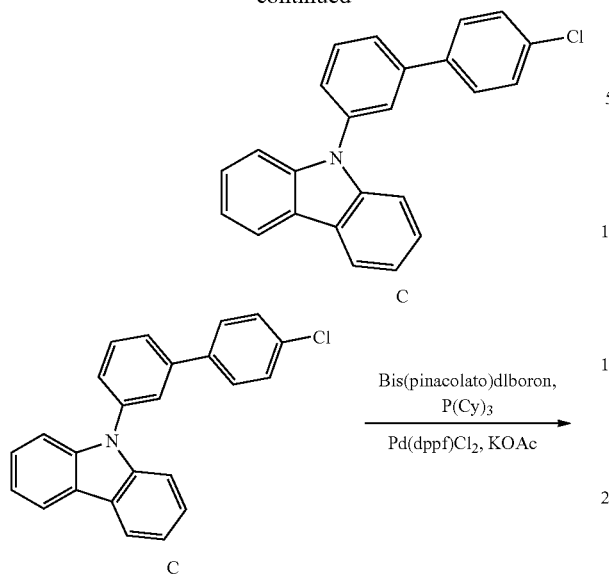

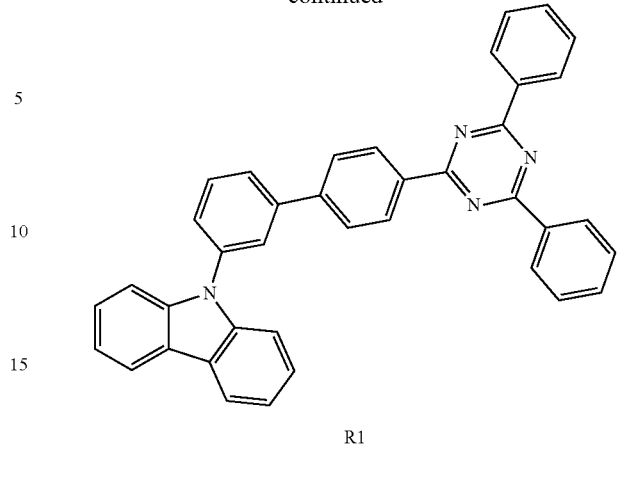

1st Step: Synthesis of Intermediate C 30.29 g (105 mmol) of 3-(9H-carbazole-9-yl)phenyl boronic acid, 20 g (105 mmol) of 1-bromo-4-chlorobenzene, 0.03 eq of Pd(PPh$_3$)$_4$, and 2 eq of K$_2$CO$_3$ were suspended in THF and distilled water and then, stirred for 12 hours. When a reaction was completed, the resultant was extracted, and an organic layer therefrom was concentrated and columned using a silica gel to obtain 35 g (Yield: 94%) of Intermediate C.

2nd Step: Synthesis of Intermediate D 35 g (100 mmol) of Intermediate C, 4.85 g (10 mmol) of Pd(dppf)Cl$_2$, 29.12 g (300 mmol) of KOAc, 30.14 g (120 mmol) of bis(pinacolato)diboron, and 6.66 g (20 mmol) of P(Cy)$_3$ were suspended in 500 ml of DMF and then, refluxed and stirred for 12 hours. When a reaction was completed, distilled water was added to the reaction solution, and the mixture was extracted/concentrated with methylene chloride and columned using a silica gel to obtain 30.8 g (Yield: 70%) of Intermediate D.

3rd Step: Synthesis of Comparative Compound R1

5.0 g (11.23 mmol) of Intermediate D, 3 g (11.23 mmol) of 2-chloro-4,6-diphenyltriazine, 0.03 eq of Pd(PPh$_3$)$_4$, and 2 eq of K$_2$CO$_3$ were suspended in THF and distilled water and then, refluxed and stirred for 12 hours. When a reaction was completed, a solid produced therein was filtered and washed with distilled water and acetone. The solid was recrystallized with monochlorobenzene to obtain 4 g (Yield: 65%) of Comparative Compound R1.

(LC/MS: theoretical value 550.65, measured value: 551.4)

Synthesis Example 4: Synthesis of Comparative Compound R2

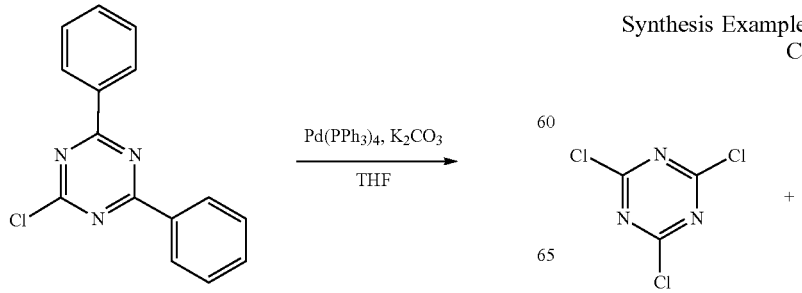

-continued

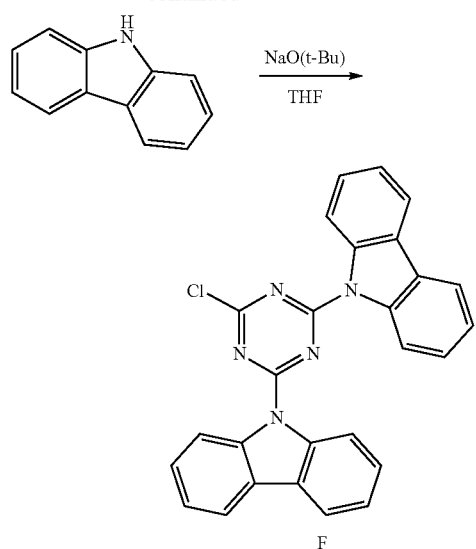

1st Step: Synthesis of Intermediate F 10 g (54.23 mmol) of cyanuric chloride and 18.13 g (108.45 mmol) of carbazole were suspended in 250 ml of THF, and 7.81 g (81.35 mmol) of NaO(t-Bu) was slowly added thereto and then, stirred for 12 hours. When a reaction was completed, a solid produced therein was filtered and washed with distilled water and acetone/hexane to obtain 12 g (Yield: 49.6%) of Intermediate F as a target compound.

2nd Step: Synthesis of Comparative Compound R2

6 g (13.46 mmol) of Intermediate F, 5.13 g (14.13 mmol) of 4-(9H-carbazole-9-yl)biphenyl boronic acid, 0.47 g (0.40 mmol) of Pd(PPh$_3$)$_4$, and 3.72 g (26.91 mmol) of K$_2$CO$_3$ were suspended in 100 ml of THF and 50 ml of distilled water and then, refluxed and stirred for 12 hours. When a reaction was completed, a solid produced therein was filtered and washed with distilled water/acetone. The obtained solid was heated and dissolved in 300 ml of dichlorobenzene and then, filtered using a silica gel, a filtrate therefrom was cooled down to room temperature, and a solid produced therein was filtered and dried to obtain 3.9 g (Yield: 40%) of Comparative Compound R2 as a target compound.

(LC/MS: theoretical value 728.84, measured value: 729.6)

Synthesis Example 5: Synthesis of Comparative Compound R3

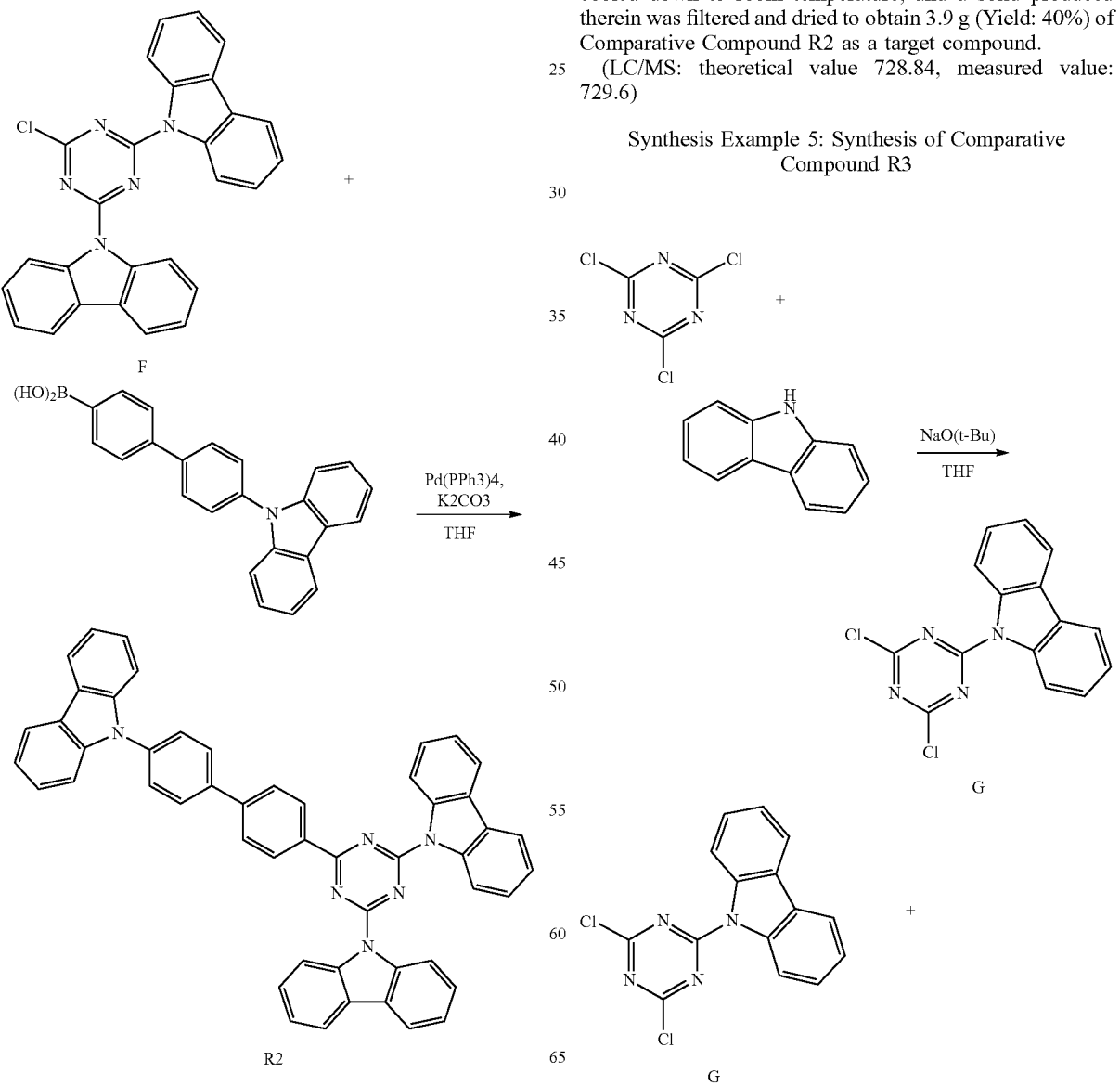

51
-continued

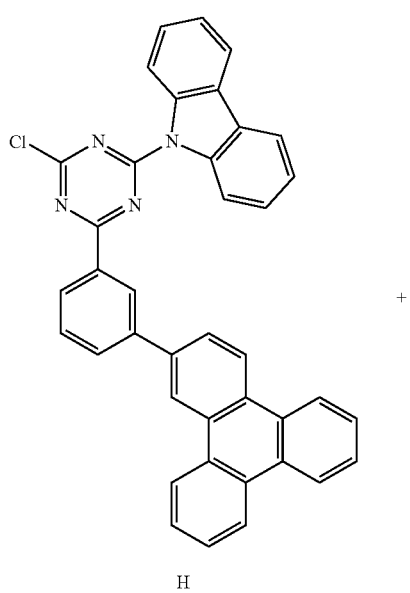

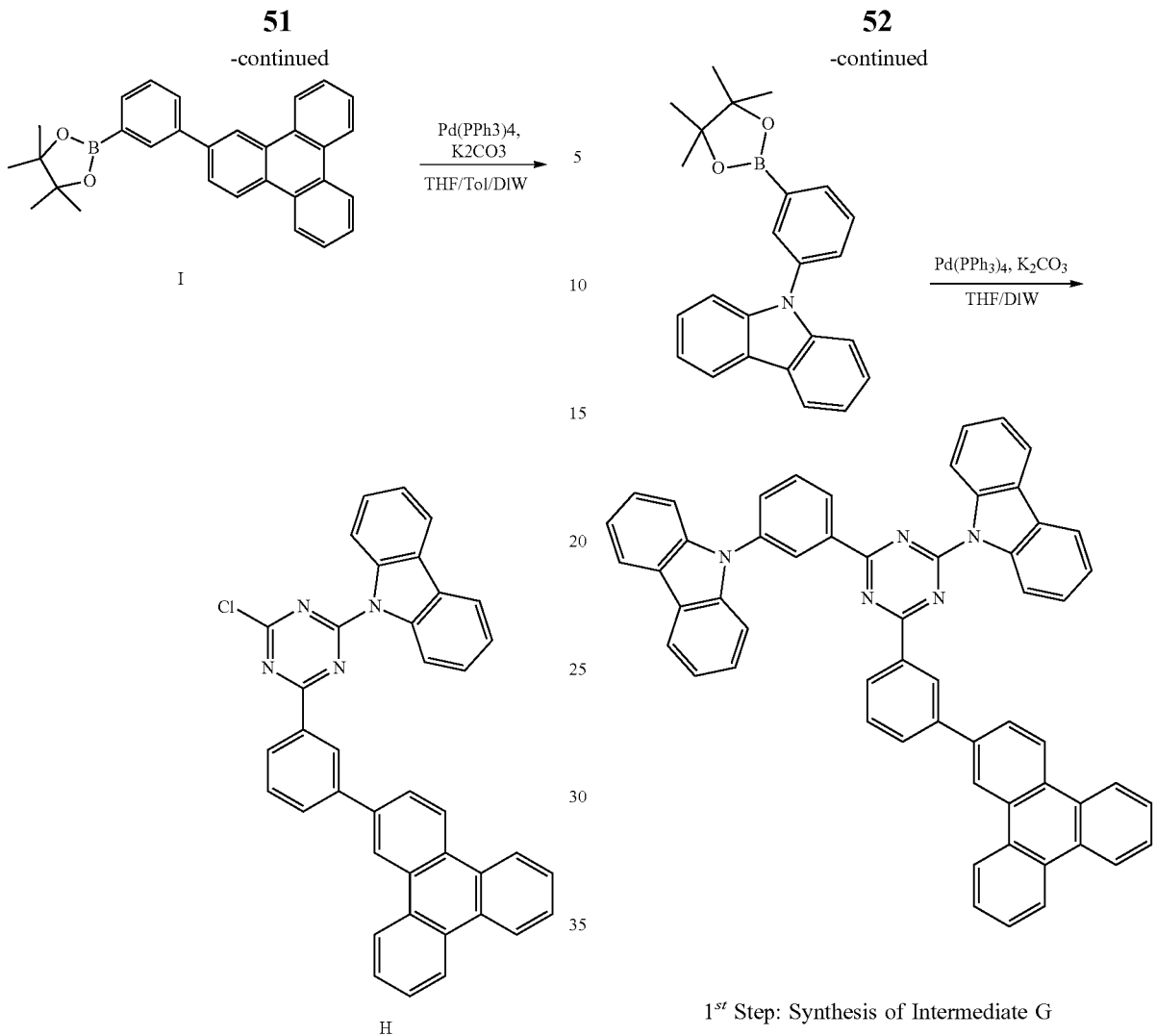

1st Step: Synthesis of Intermediate G 36.9 g (200 mmol) of cyanuric chloride and 33.4 g (200 mmol) of carbazole were suspended in 300 ml of THF, 19.22 g (200 mmol) of NaO(t-Bu) was slowly added thereto at 0° C. When a reaction was completed, a solid produced therein was filtered and washed with distilled water/acetone/hexane to obtain 10 g (Yield: 16%) of Intermediate G.

2nd Step: Synthesis of Intermediate H 4.9 g (15.55 mmol) of Intermediate G, 6.69 g (15.55 mmol) of Intermediate I (refer to Synthesis Example 3 of Korean Patent Laid-Open Publication No. 10-2014-0135524), 0.89 g (0.78 mmol) of Pd(PPh$_3$)$_4$, and 5.37 g (38.87 mmol) of K$_2$CO$_3$ were suspended in 50 ml of THF/50 ml of toluene/50 ml of distilled water and then, refluxed and stirred. When a reaction was completed, a solid produced therein was filtered, washed with distilled water/acetone, and dried to obtain 5 g (Yield: 56%) of Intermediate H.

3rd Step: Synthesis of Comparative Compound R3

2.4 g (4.11 mmol) of Intermediate H, 1.67 g (4.53 mmol) of 9-[3-(4,4,5,5-tetramethyl-1,3,2-dioxaborolan-2-yl)phenyl]-9H-carbazole, 0.14 g (0.12 mmol) of Pd(PPh$_3$)$_4$, and 1.14 g (8.23 mmol) of K$_2$CO$_3$ were suspended in 50 ml of THF and 50 ml of DIW and then, refluxed and stirred for 12 hours. When a reaction was completed, a solid produced therein was filtered and washed with distilled water and acetone. The solid was heated and dissolved in 100 ml of dichlorobenzene and filtered using a silica gel, and a filtrate therefrom was cooled down to room temperature. A solid produced in the filtrate was filtered and washed with acetone to obtain 2.94 g (Yield: 89.5%) of Comparative Compound R3.

(LC/MS: theoretical value 789.92, measured value: 790.40)

Synthesis Example 6: Synthesis of Comparative Compound R4

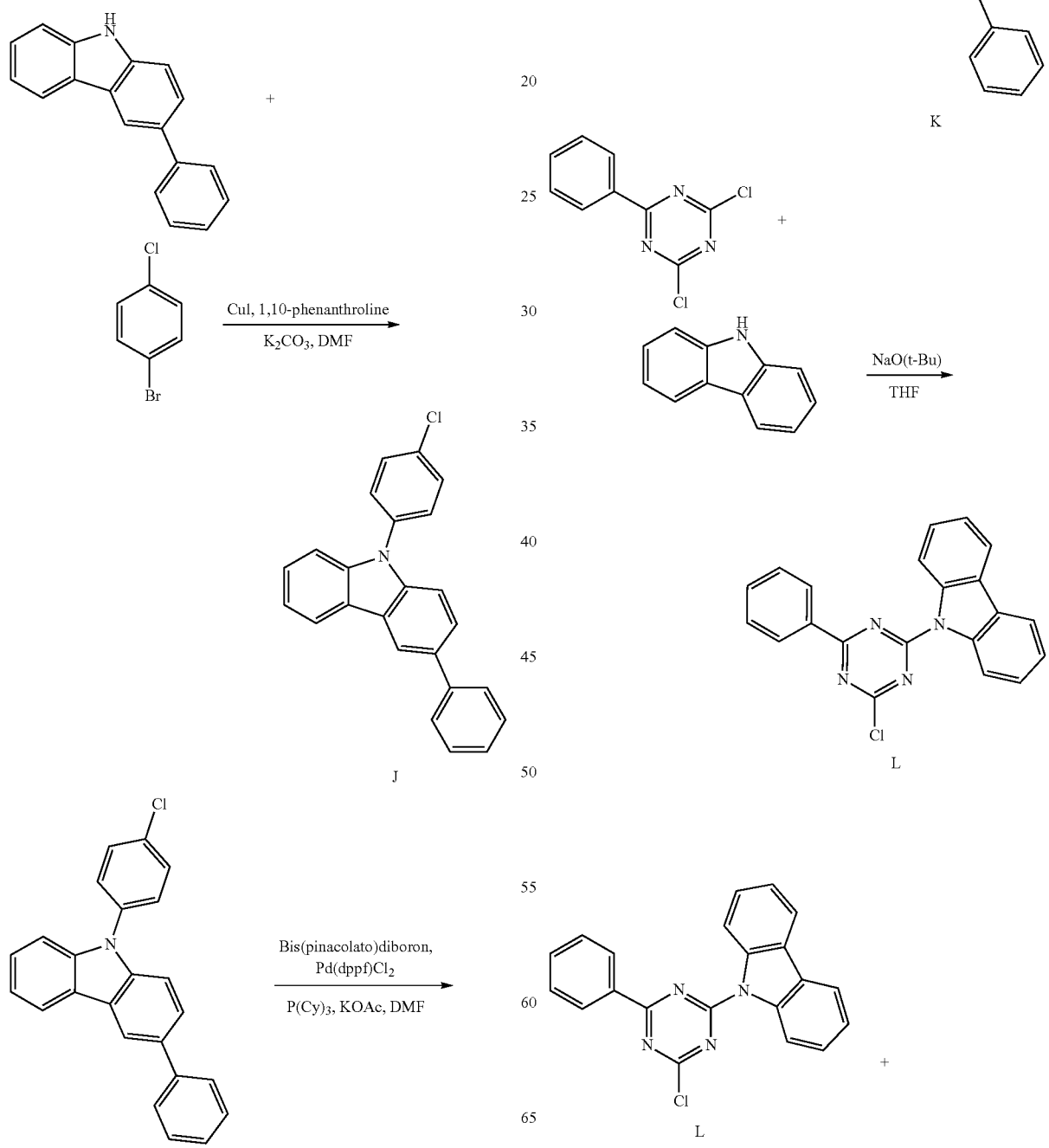

-continued

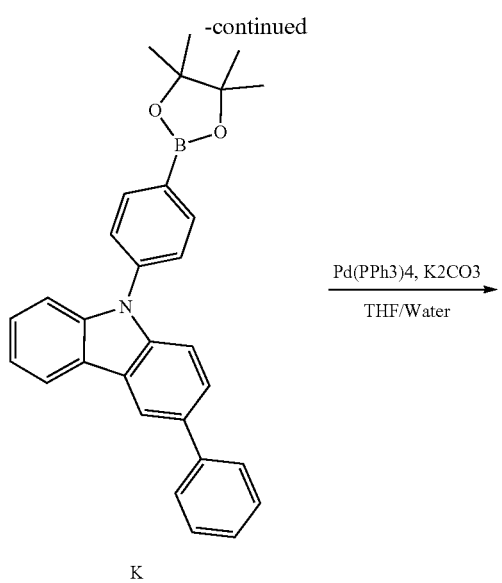

K

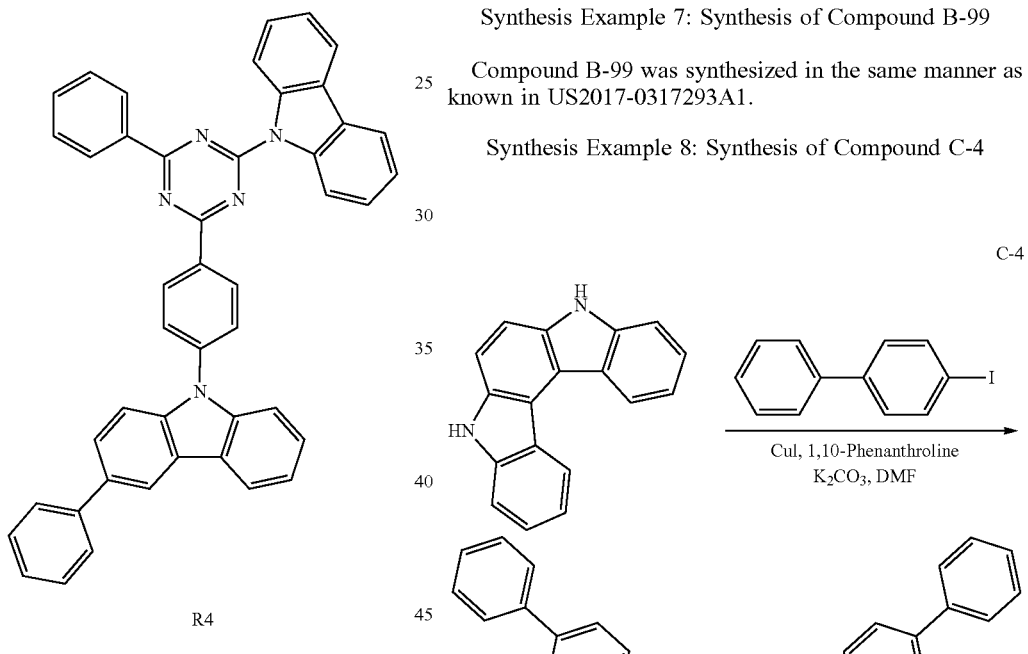

R4

1st Step: Synthesis of Intermediate J 30 g (123.30 mmol) of 3-phenyl-9H-carbazole, 30.69 g (160.30 mmol) of 1-bromo-4-chlorobenzene, 4.70 g (24.66 mmol) of CuI, 51.13 g (369.91 mmol) of $K_2CO_3$, and 4.44 g (24.66 mmol) of 1,10-phenanthroline were suspended in 300 ml of DMF and then, refluxed and stirred for 12 hours. When a reaction was completed, the resultant was cooled down to room temperature, distilled water was added thereto, and the mixture was extracted and concentrated with toluene. A product therefrom was columned using a silica gel to obtain 21 g (Yield: 48%) of Intermediate J.

2nd Step: Synthesis of Intermediate K 10.6 g (Yield: 39%) of Intermediate K was synthesized according to the same method as the 2nd step of Synthesis Example 3 except that 21 g (59.35 mmol) of Intermediate J was used.

3rd Step: Synthesis of Intermediate L 58.81 g (260.15 mmol) of 2-phenyl-4,6-dichlorotriazine and 30 g (179.42 mmol) of carbazole were suspended in 500 ml of THF, and 18.11 g of NaO(t-Bu) was slowly added thereto and then, stirred at room temperature for 12 hours. When a reaction was completed, a solid produced therein was filtered, washed with distilled water and acetone, and dried to obtain 40 g (Yield: 62.5%) of Intermediate L.

4th Step: Synthesis of Comparative Compound R4

8 g (Yield: 53.5%) of Comparative Compound R4 was obtained according to the same method as the 2nd step of Synthesis Example 1 except that 8.34 g (23.37 mmol) of Intermediate L and 10.62 g (23.84 mmol) of Intermediate K were used.

(LC/MS: theoretical value 639.75, measured value: 640.52)

(Preparation of Second Compound for Organic Optoelectronic Device)

Synthesis Example 7: Synthesis of Compound B-99

Compound B-99 was synthesized in the same manner as known in US2017-0317293A1.

Synthesis Example 8: Synthesis of Compound C-4

8 g (31.2 mmol) of 5,8-dihydroindolo[2,3-c]carbazole (CAS No.: 200339-30-6), 20.5 g (73.32 mmol) of 4-iodo-biphenyl, 1.19 g (6.24 mmol) of CuI, 1.12 g (6.24 mmol) of 1,10-phenanthoroline, and 12.9 g (93.6 mmol) of $K_2CO_3$ were put in a round-bottomed flask, and 50 ml of DMF was added thereto and then, refluxed and stirred under a nitrogen atmosphere for 24 hours. When a reaction was completed, distilled water was added thereto to precipitate solids, and the solids were filtered. The solids therefrom were dissolved in 250 ml of xylene, filtered using a silica gel, and precipitated as white solids to obtain 16.2 g (Yield: 93%) of Compound C-4.

LC/MS calculated for: C42H28N2 Exact Mass: 560.2252
found for: 561.23

(Manufacture of Organic Light Emitting Diode)

Example 1

A glass substrate coated with ITO (Indium tin oxide) with a thickness of 1500 Å was washed with distilled water. After washing with the distilled water, the glass substrate was washed with a solvent such as isopropyl alcohol, acetone, methanol, and the like ultrasonically and dried and then, moved to a plasma cleaner, cleaned by using oxygen plasma for 10 minutes, and moved to a vacuum depositor. This obtained ITO transparent electrode was used as an anode, Compound A was vacuum-deposited on the ITO substrate to form a 700 Å-thick hole injection layer, and Compound B was deposited to be 50 Å-thick on the injection layer, and then Compound C was deposited to be 1020 Å-thick to form a hole transport layer. On the hole transport layer, 400 Å-thick light emitting layer was formed by vacuum-depositing Compound 2 of Synthesis Example 1 as a host and doping 7 wt % of PhGD as a dopant. Subsequently, on the light emitting layer, a 300 Å-thick electron transport layer was formed by simultaneously vacuum-depositing Compound D and Liq in a ratio of 1:1, and on the electron transport layer, Liq and Al were sequentially vacuum-deposited to be 15 Å-thick and 1,200 Å-thick, producing an organic light emitting diode.

The organic light emitting diode had a multi-layered organic thin layer, and specifically the following structure.

ITO/Compound A (700 Å)/Compound B (50 Å)/Compound C (1020 Å)/EML[Compound 2:PhGD (7 wt %)](400 Å)/Compound D:Liq (300 Å)/Liq (15 Å)/Al (1200 Å).

- Compound A: N4,N4'-diphenyl-N4,N4'-bis(9-phenyl-9H-carbazol-3-yl)biphenyl-4,4'-diamine
- Compound B: 1,4,5,8,9,11-hexaazatriphenylene-hexacarbonitrile (HAT-CN),
- Compound C: N-(biphenyl-4-yl)-9,9-dimethyl-N-(4-(9-phenyl-9H-carbazol-3-yl)phenyl)-9H-fluoren-2-amine
- Compound D: 8-(4-(4,6-di(naphthalen-2-yl)-1,3,5-triazin-2-yl)phenyl)quinoline

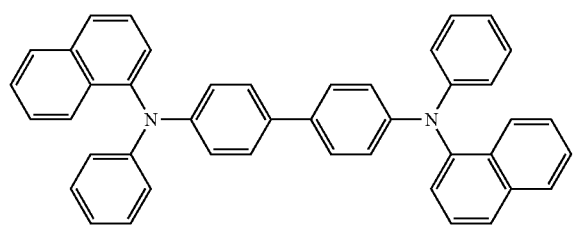

[NPB]

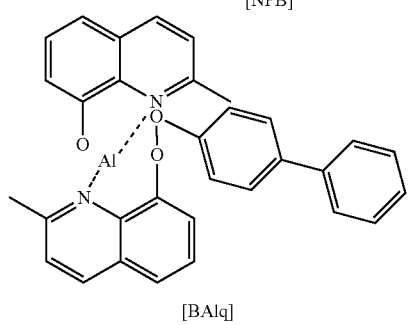

[BAlq]

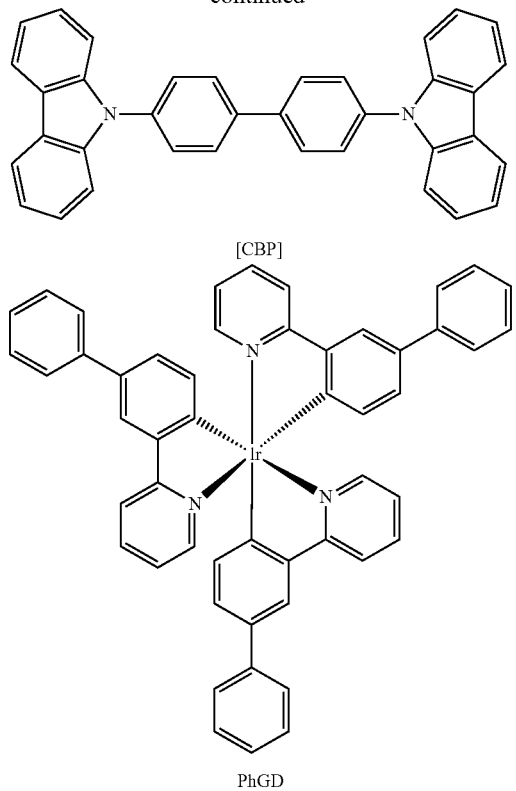

[CBP]

PhGD

Examples 2 to 11 and Comparative Examples 1 to 6

The diodes of Example 2 to Example 11, and Comparative Example 1 to Comparative Example 6 were manufactured in the same manner as in Example 1, except that the host was changed as described in Tables 1 to 6.

Evaluation: Effect of Increasing Life-Span

The driving voltages and life-span characteristics of the organic light emitting diodes according to Examples 1 to 11, and Comparative Examples 1 to 6 were evaluated. Specific measurement methods are as follows, and the results are shown in Tables 1 to 6.

(1) Measurement of Life-Span

T90 life-spans of the organic light emitting diodes according to Examples 1 to 11 and Comparative Examples 1 to 6 were measured as a time when their luminance decreased down to 90% relative to the initial luminance (cd/m²) after emitting light with 24000 cd/m² as the initial luminance (cd/m²) and measuring their luminance decrease depending on a time with a Polanonix life-span measurement system.

(2) Calculation of T90 Life-Span Ratio (%)

The relative comparison values of T90(h) of the single host or mixed host example applying the same second host (applying the first compound as the first host) and the mixed host comparative example (applying the comparative compound as the first host) are shown.

$T90$ life-span ratio (%)={[$T90(h)$ of the example (the first compound was used as a single or mixed host)/[$T90(h)$ of the comparative example (the comparative compound was used as a single or mixed host)]}×100

TABLE 1

| | Host | T90 life-span ratio (%) |
|---|---|---|
| Example 1 | Compound 2 | 200% |
| Example 2 | Compound 7 | 195% |
| Comparative Example 1 | Comparative Compound R1 | 100% |

TABLE 2

| | Host | T90 life-span ratio (%) |
|---|---|---|
| Example 3 | Compound 2 | 400% |
| Example 4 | Compound 7 | 380% |
| Comparative Example 2 | Comparative Compound R2 | 100% |

TABLE 3

| | Host | T90 life-span ratio (%) |
|---|---|---|
| Example 5 | Compound 2 | 210% |
| Example 6 | Compound 7 | 194% |
| Comparative Example 3 | Comparative Compound R3 | 100% |

TABLE 4

| | Host | T90 life-span ratio (%) |
|---|---|---|
| Example 7 | Compound 2 | 130% |
| Example 8 | Compound 7 | 129% |
| Comparative Example 4 | Comparative Compound R4 | 100% |

TABLE 5

| | Host | | First, second host ratio | T90 life-span ratio (%) |
|---|---|---|---|---|
| | First host | Second host | | |
| Example 9 | Compound 2 | Compound B-99 | 3:7 | 160% |
| Example 10 | Compound 7 | Compound B-99 | 3:7 | 150% |
| Comparative Example 5 | Comparative Compound R1 | Compound B-99 | 3:7 | 100% |

TABLE 6

| | Host | | First, second host ratio | T90 life-span ratio (%) |
|---|---|---|---|---|
| | First host | Second host | | |
| Example 11 | Compound 2 | Compound C-4 | 5:5 | 140% |
| Comparative Example 6 | Comparative Compound R1 | Compound C-4 | 5:5 | 100% |

Referring to Tables 1 to 6, the life-span of the organic light emitting diodes according to Examples 1 to 11 is significantly improved compared with the organic light emitting diodes according to Comparative Examples 1 to 6.

While this invention has been described in connection with what is presently considered to be practical embodiments, it is to be understood that the invention is not limited to the disclosed embodiments, but, on the contrary, is intended to cover various modifications and equivalent arrangements included within the spirit and scope of the appended claims.

The invention claimed is:

1. A compound for an organic optoelectronic device, the compound being represented by Chemical Formula 1:

[Chemical Formula 1]

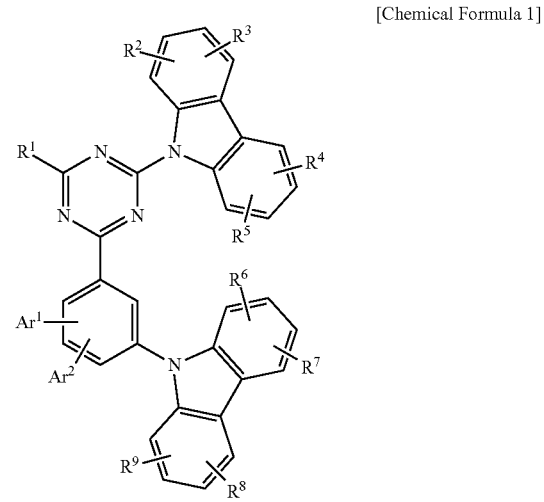

wherein, in Chemical Formula 1, $R^1$ is a phenyl group that is unsubstituted or substituted with a C6 to C12 aryl group, a biphenyl group that is unsubstituted or substituted with a C6 to C12 aryl group, a fluorenyl group that is unsubstituted or substituted with a C6 to C12 aryl group, a dibenzofuranyl group that is unsubstituted or substituted with a C6 to C12 aryl group or a dibenzothiophenyl group that is unsubstituted or substituted with a C6 to C12 aryl group, $R^2$ to $R^9$ are each independently hydrogen, deuterium, a cyano group, a halogen, a substituted or unsubstituted amine group, a substituted or unsubstituted C1 to C30 alkyl group, a substituted or unsubstituted C6 to C30 aryl group, a substituted or unsubstituted C2 to C30 heterocyclic group, or a combination thereof, and $Ar^1$ and $Ar^2$ are each independently hydrogen, deuterium, or a substituted or unsubstituted C6 to C20 aryl group.

2. The compound of claim 1, wherein $R^1$ is a group of Group I:

[Group 1]

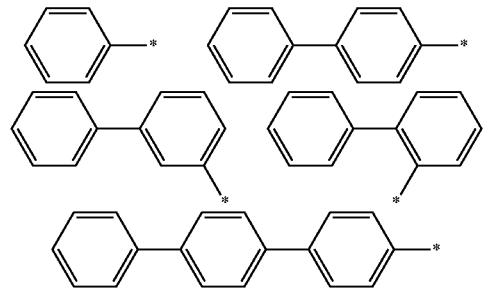

-continued

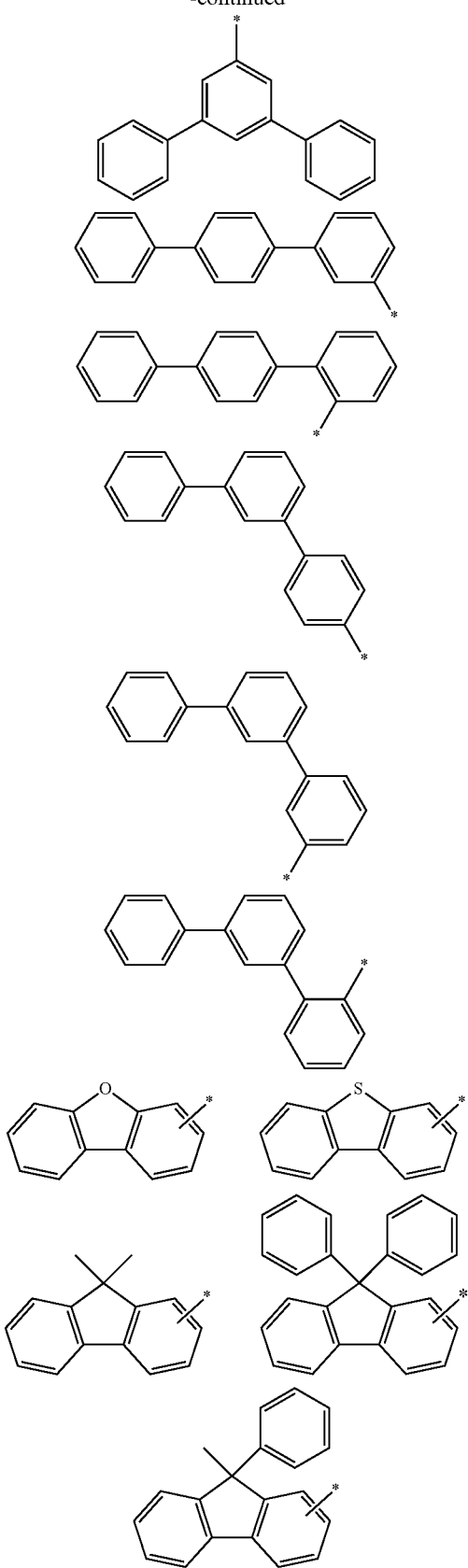

wherein, in Group I, * is a linking point.

3. The compound of claim 1, wherein $R^2$ to $R^5$ are each independently hydrogen, deuterium, or a substituted or unsubstituted C6 to C12 aryl group.

4. The compound of claim 1, wherein $R^6$ to $R^9$ are each independently hydrogen, deuterium, or a substituted or unsubstituted C6 to C12 aryl group.

5. The compound of claim 1, wherein $Ar^1$ and $Ar^2$ are each independently hydrogen, deuterium, or a substituted or unsubstituted C6 to C12 aryl group.

6. The compound of claim 1, wherein the compound is a compound of Group 1:

[Group 1]

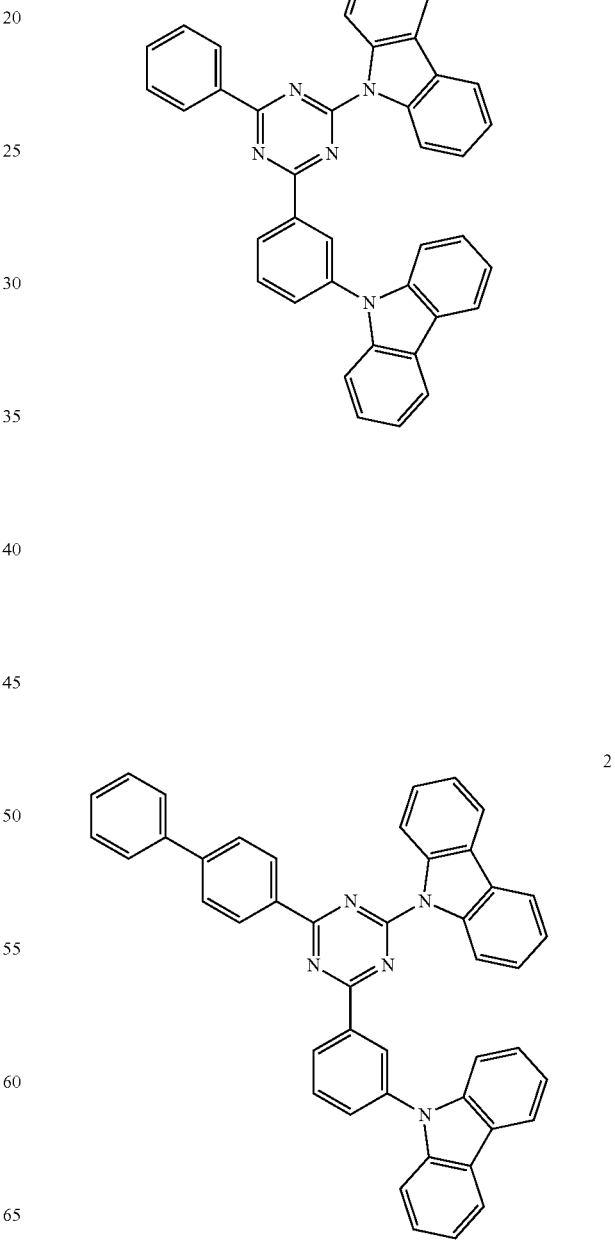

3
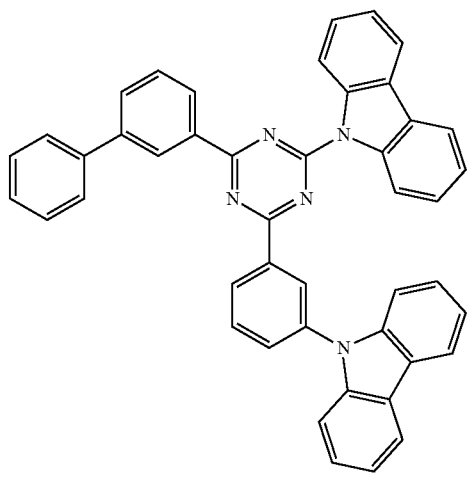
4
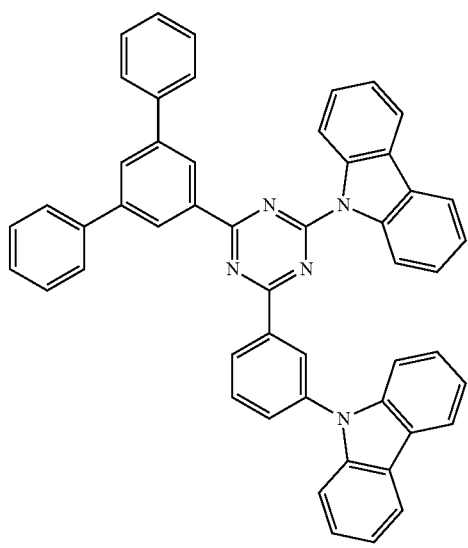
5
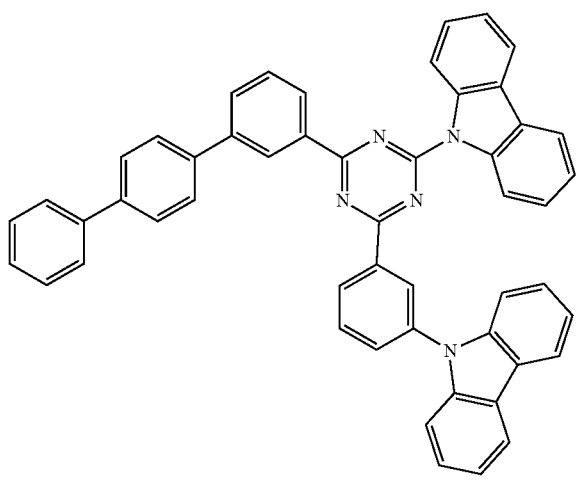
6
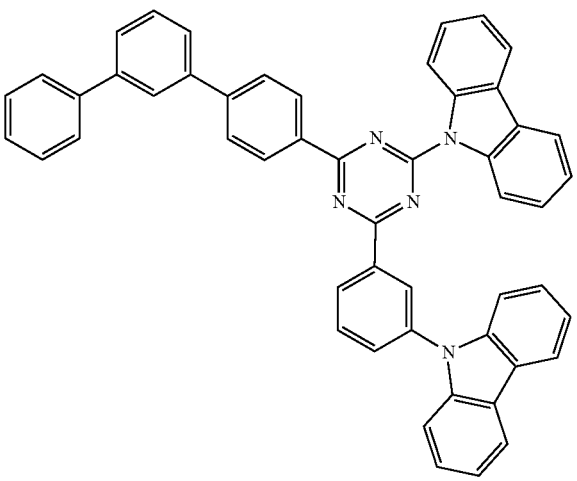
7
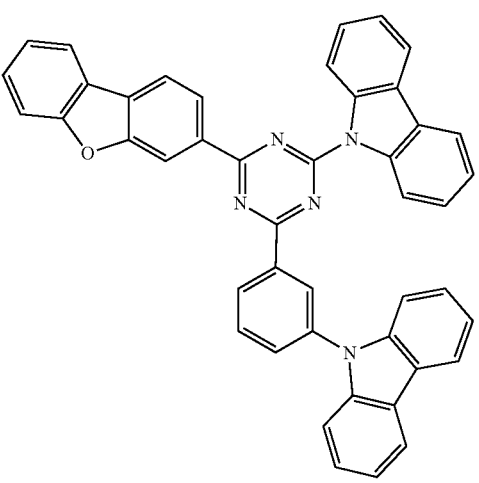
8
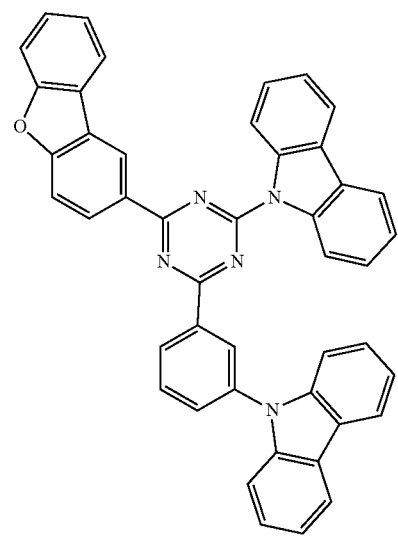

9
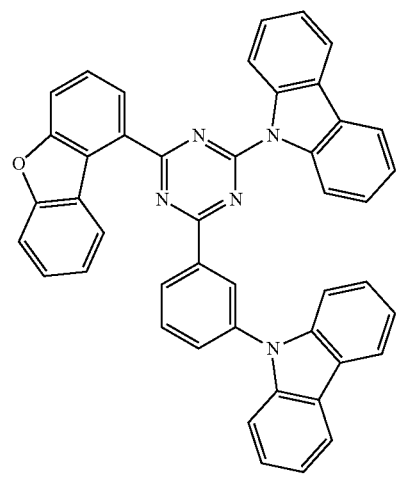
10
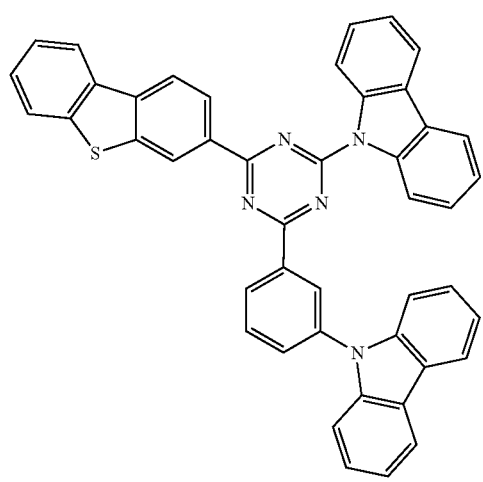
11
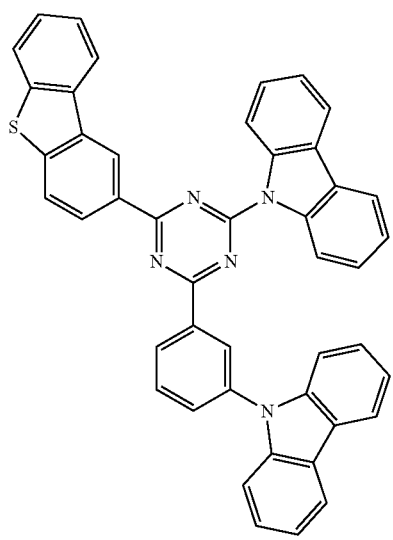
12
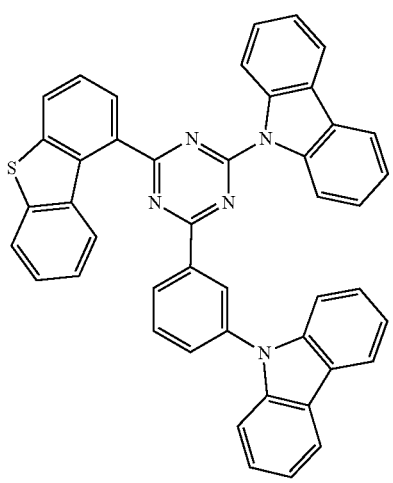
13
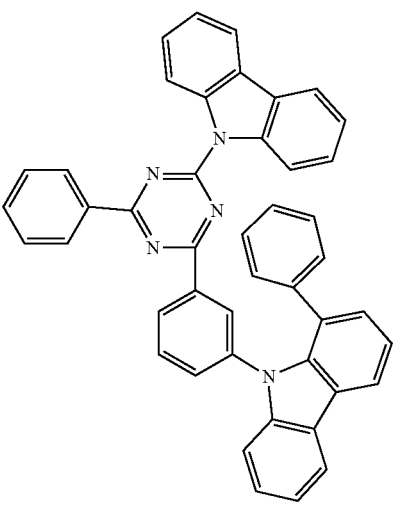
14
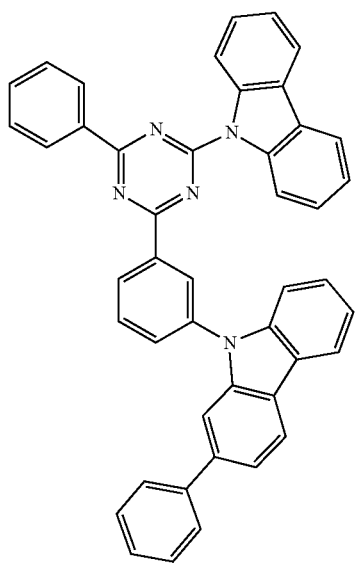

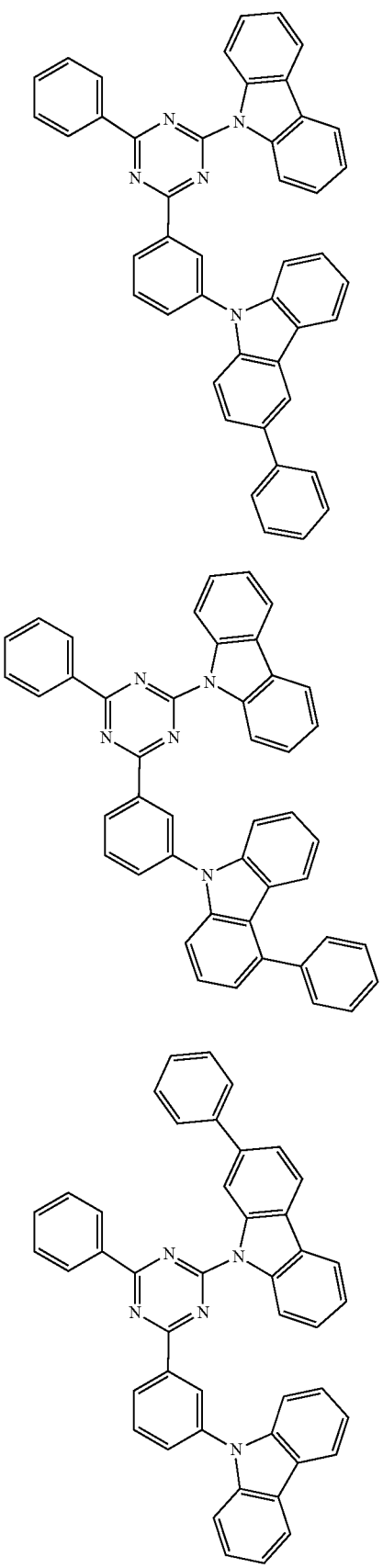
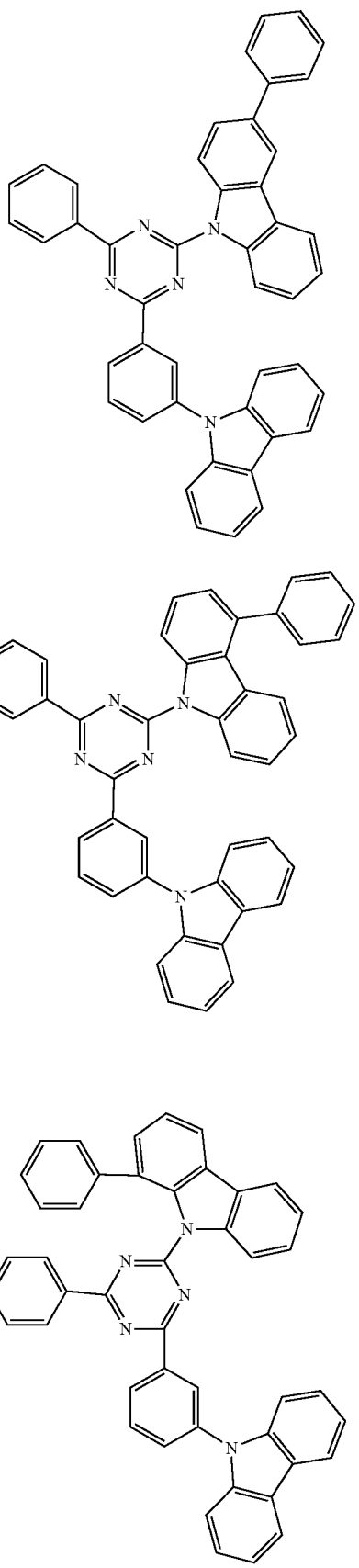

22
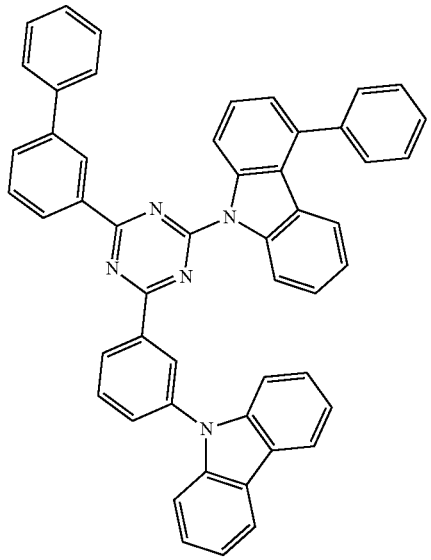
23
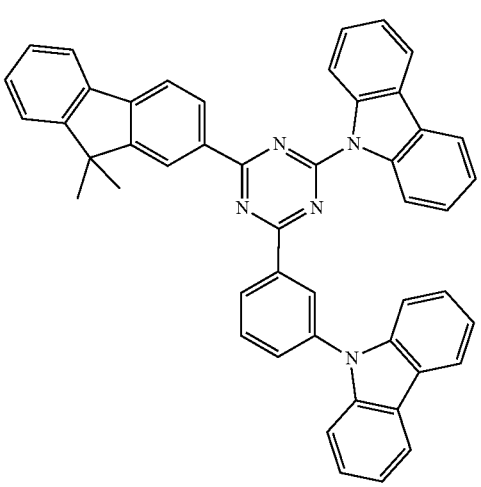
24
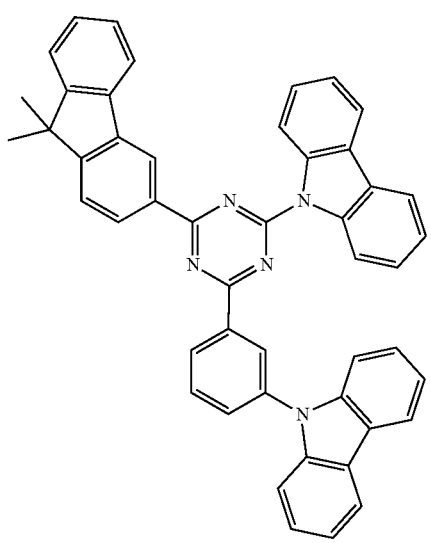
25
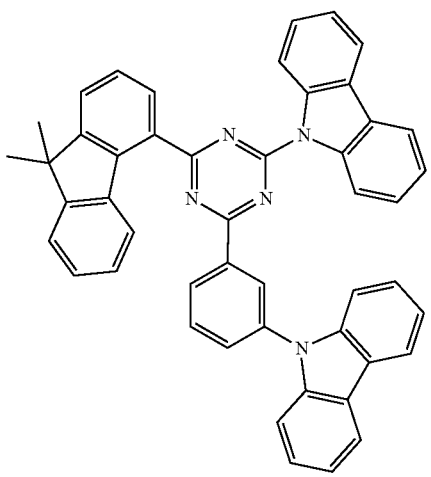
26
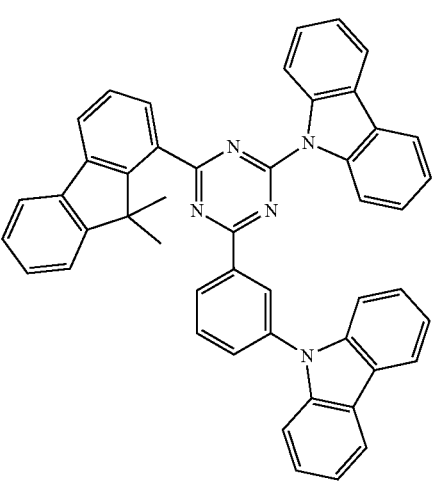
27
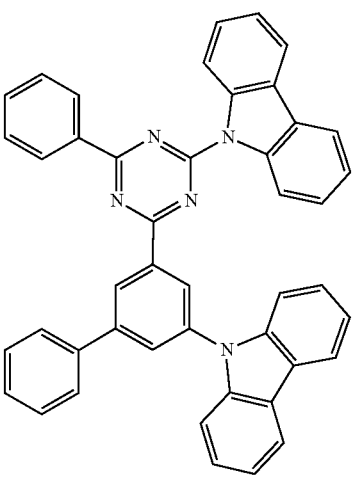

-continued

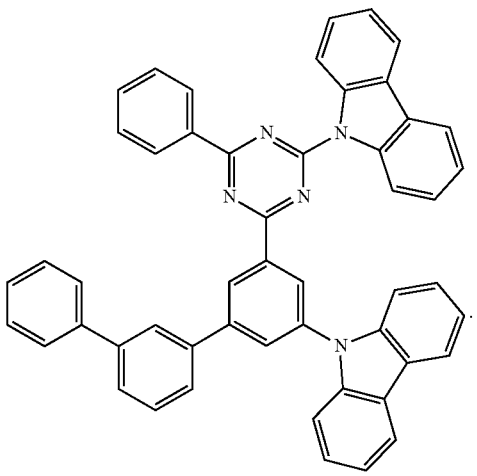

28

7. An organic optoelectronic device, comprising:
an anode and a cathode facing each other,
at least one organic layer disposed between the anode and the cathode,
wherein the at least one organic layer comprises the compound for the organic optoelectronic device of claim 1.

8. The organic optoelectronic device of claim 7, wherein
the at least one organic layer comprises a light emitting layer, and
the light emitting layer comprises the compound for an organic optoelectronic device.

9. A display device comprising the organic optoelectronic device of claim 7.

* * * * *